(12) United States Patent
Gaeta et al.

(10) Patent No.: US 7,702,381 B2
(45) Date of Patent: Apr. 20, 2010

(54) OPTICAL FIBER DELIVERY AND COLLECTION METHOD FOR BIOLOGICAL APPLICATIONS SUCH AS MULTIPHOTON MICROSCOPY, SPECTROSCOPY, AND ENDOSCOPY

(75) Inventors: Alexander L. Gaeta, Ithaca, NY (US);
Dimitre G. Ouzounov, Ithaca, NY (US);
Watt W. Webb, Ithaca, NY (US);
Rebecca M. Williams, Ithaca, NY (US);
Warren R. Zipfel, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/918,950

(22) Filed: Aug. 16, 2004

(65) Prior Publication Data

US 2005/0043636 A1    Feb. 24, 2005

Related U.S. Application Data

(60) Provisional application No. 60/496,241, filed on Aug. 19, 2003.

(51) Int. Cl.
*A61B 5/00* (2006.01)
(52) U.S. Cl. ...................................... 600/478; 385/125
(58) Field of Classification Search ................. 600/478, 600/472, 407; 385/33, 37, 125
See application file for complete search history.

(56) References Cited

U.S. PATENT DOCUMENTS 4,576,173 A    3/1986   Parker et al.
4,592,361 A    6/1986   Parker et al.
4,895,156 A    1/1990   Schulze
5,034,613 A    7/1991   Denk et al.
5,115,137 A    5/1992   Andersson-Engels et al.
5,119,815 A    6/1992   Chance (Continued)

FOREIGN PATENT DOCUMENTS

EP    0 512 965 A1    11/1992

(Continued)

OTHER PUBLICATIONS

Arendt et al., "Investigation of Early Cancerous Changes in Bladder Tissue by Autofluorescence," *Proceedings—19th International Conference—IEEE/EMBS* pp. 2290-2293 (1997).

(Continued)

*Primary Examiner*—Brian Casler
*Assistant Examiner*—Parikha S Mehta
(74) *Attorney, Agent, or Firm*—Nixon Peabody LLP

(57) ABSTRACT

The present invention is directed to a method of applying radiation through an optical fiber for detecting disease within a plant or animal or other penetrable tissue, or imaging a particular tissue of a plant or animal. In addition, fluorescence and nonlinear scattering signals can be detected and localized within a subject by such application of radiation through an optical fiber. The radiation is effective to promote simultaneous multiphoton excitation. The optical fibers are used alone to examine internal regions of tissue, in conjunction with an optical biopsy needle to evaluate sub-surface tissue, or with an endoscope to evaluate tissue within body cavities. The present invention also relates to a device for coupling in radiation from an ultrashort mode-locked laser into the beam path of a microscope.

91 Claims, 14 Drawing Sheets

U.S. PATENT DOCUMENTS

| | | | |
|---|---|---|---|
| 5,127,405 A | 7/1992 | Alcala et al. | |
| 5,197,470 A | 3/1993 | Helfer et al. | |
| 5,311,013 A | 5/1994 | Gutcheck et al. | |
| 5,323,775 A | 6/1994 | Joshi et al. | |
| 5,333,044 A | 7/1994 | Shaffer | |
| 5,341,805 A | 8/1994 | Stavridi et al. | |
| 5,353,790 A | 10/1994 | Jacques et al. | |
| 5,419,323 A | 5/1995 | Kittrell et al. | |
| 5,421,337 A | 6/1995 | Richards-Kortum et al. | |
| 5,579,773 A | 12/1996 | Vo-Dinh et al. | |
| 5,590,660 A | 1/1997 | MacAulay et al. | |
| 5,628,310 A | 5/1997 | Rao et al. | |
| 5,697,373 A | 12/1997 | Richards-Kortum et al. | |
| 5,699,795 A | 12/1997 | Richards-Kortum et al. | |
| 5,812,729 A * | 9/1998 | Allison et al. | 385/142 |
| 5,827,190 A | 10/1998 | Palcic et al. | |
| 5,862,287 A | 1/1999 | Stock et al. | |
| 5,986,271 A | 11/1999 | Lazarev et al. | |
| 5,995,281 A | 11/1999 | Simon et al. | |
| 6,070,096 A | 5/2000 | Hayashi | |
| 6,178,041 B1 | 1/2001 | Simon | |
| 6,201,989 B1 | 3/2001 | Whitehead et al. | |
| 6,212,425 B1 | 4/2001 | Irion et al. | |
| 6,236,779 B1 | 5/2001 | Kafka et al. | |
| 6,238,348 B1 | 5/2001 | Crowley et al. | |
| 6,249,630 B1 | 6/2001 | Stock et al. | |
| 6,320,191 B1 * | 11/2001 | Rudd | 250/341.1 |
| 6,356,088 B1 | 3/2002 | Simon et al. | |
| 6,389,198 B2 | 5/2002 | Kafka et al. | |
| 6,580,941 B2 | 6/2003 | Webb | |
| 6,621,953 B1 | 9/2003 | Ulrich et al. | |
| 6,690,511 B2 | 2/2004 | Engelhardt et al. | |
| 6,690,966 B1 * | 2/2004 | Rava et al. | 600/473 |
| 6,710,918 B2 | 3/2004 | Birk et al. | |
| 6,839,586 B2 | 1/2005 | Webb | |
| 6,961,599 B2 * | 11/2005 | Lambert et al. | 600/318 |
| 2002/0028044 A1 * | 3/2002 | Birk et al. | 385/43 |
| 2003/0100824 A1 * | 5/2003 | Warren et al. | 600/407 |
| 2004/0028356 A1 * | 2/2004 | Birks et al. | 385/122 |
| 2004/0086245 A1 * | 5/2004 | Farroni et al. | 385/123 |
| 2004/0247271 A1 * | 12/2004 | Skovgaard et al. | 385/125 |
| 2005/0024716 A1 * | 2/2005 | Nilsson et al. | 359/341.31 |

FOREIGN PATENT DOCUMENTS

| | | |
|---|---|---|
| EP | 0 920 831 A1 | 6/1999 |
| GB | 2300045 A | 10/1996 |

OTHER PUBLICATIONS

Atherton et al., "Pre-Chirped Fiber Transport of 800nm 100 fs Pulses," in *Commercial Applications of Ultrafast Lasers*, M.K. Reed, ed., *Proc. SPIE* 3269:22-25 (1998).

Birks et al., "Full 2-D Photonic Bandgaps in Silica/Air Structures," *Electron. Lett.* 31(22):1941-1943 (1995).

Clark et al., "Fiber Delivery of Femtosecond Pulses from a Ti:Sapphire Laser," *Optics Letters* 26(17):1320-1322 (2001).

Crystal Fibre A/S—Website descriptions of photonics crystal fiber products (http://www/crystal-fiber.com) (printed Jun. 17, 2003).

Denk et al., "Two-Photon Molecular Excitation in Laser-Scanning Microscopy," in J.B. Pawley, ed., *Handbook of Biological Confocal Microscopy*, New York: Plenum Press, pp. 445-458 (1995).

Dinkel et al., "Remote Two-Photon Excited Fluorescence Sensing in a Simulated Fermentation Broth," *Analytica Chimica Acta* 263:131-136 (1992).

Glanzmann et al., "Time-Resolved Spectrofluorometer for Clinical Tissue Characterization During Endoscopy," *Review of Scientific Instruments* 70(10):4067-4077 (1999).

Helmchen et al., "A Miniaturized Two-Photon Fiber-Scanning Microscope for In Vivo Imaging," *Society for Neuroscience* 25:322.1 (1999) (Abstract).

Helmchen et al., "Enhanced Two-Photon Excitation Through Optical Fiber by Single-Mode Propagation in a Large Core," *Appl. Opt.* 41:2930-2934 (2002).

Knight et al., "Photonic Band Gap Guidance in Optical Fibers," *Science* 282:1476-1478 (1998).

Lago et al., "Two-Photon-Induced Fluorescence of Biological Markers Based on Optical Fibers," *Optics Letters* 20(20):2054-2056 (1995).

Maiti et al., "Multiphoton Fluorescence Spectroscopy Through Optical Fibers," *Biophys. J.* 72:A217 (1997) (Abstract).

Maiti et al., "Measuring Serotonin Distribution in Live Cells with Three-Photon Excitation," *Science* 275:530-532 (1997).

Masters et al., "Multiphoton Excitation Microscopy of Human Skin In Vivo: Early Development of an Optical Biopsy," in *SFM99* (Saratov Fall Meeting 99), Saratov State University Optics Department, Russia (1999).

Masters, B.R., "Confocal Microscopy and Multi-Photon Excitation Microscopy of Human Skin In Vivo," *Optics Express* 8(1):2-10 (2001).

Myaing et al., "Nonlinear Propagation of Negatively Chirped Pulses: Maximizing the Peak Intensity at the Output of a Fiber Probe," *Optics Express* 7(5):210-214 (2000).

Nichols et al., "Identification of the Principle Sources of Two-Photon Autofluorescence From HeLa Cell Monolayers," *Biophys. J.* 72:A346 (1997) (Abstract).

Nichols et al., "Visualization of Mitochondria Via Two-Photon Microscopy of NADH: Identifying Conditions that Maintain Cell Viability," *Biophys. J.* 76:A9 (1999) (Abstract).

Ouzounov et al., "Delivery of Nanojoule Femtosecond Pulses Through Large-Core Microstructured Fibers," *Optics Letters* 27(17):1513-1515 (2002).

Ouzounov et al., "Dispersion Measurements of Microstructured Fibers Using Femtosecond Laser Pulses," *Optics Communications* 192:219-223 (2001).

Ranka et al., "Optical Properties of High-Delta Air-Silica Microstructure Optical Fibers," *Optics Letters* 25(11):796-798 (2000).

Shear et al., "Multiphoton-Excited Visible Emission by Serotonin Solutions," *Photochemistry and Photobiology* 65(6):931-936 (1997).

Shear et al., "Multiphoton-Excited Photochemistry Yields Visible Emission from Serotonin," *Biophys. J.* 72:A346 (1997) (Abstract).

Treacy, E.B., "Optical Pulse Compression with Diffraction Gratings," *IEEE J. Quantum Electron.* 5(9):454-458 (1969).

Tromberg et al., "Optical Fiber Fluoroprobes for Biological Measurements," *Applied Spectroscopy* 38(1):38-42 (1984).

Webb et al., "Multiphoton Molecular Excitation to Illuminate Non-Linear Laser Microscopy," in Barbara et al., eds., *Ultrafast Phenomena X*, Springer Series in Chemical Physics, vol. 62, Berlin: Springer-Verlag, p. 133 (1996) (Abstract).

Webb, W.W., "Biological Applications of Nonlinear Laser Microscopy," *Advanced Solid-State Lasers*, Twelfth Topical Meeting p. 65 (1997) (Abstract).

Webb, W.W., "Multiphoton Fluorescence Correlation Spectroscopy with Single Molecules in Living Cells," 4th International Weber Symposium on Innovative Fluorescence Methodologies in Biochemistry and Medicine (1999) (Abstract).

Webb, W.W., "Non-Linear Laser Microscopy," *Photochemistry and Photobiology* 63:45S (1996) (Abstract).

Webb, W.W., "Non-Linear Laser Microscopy," *Progress in Biophysics & Molecular Biology* XIIth International Biophysics Congress, 65:20 (1996) (Abstract).

Webb, W.W., "Non-Linear Optical Microscopy," *Biophys. J.* 70:A429 (1996) (Abstract).

Williams et al., "Mucosal Mast Cell Secretion Processes Imaged Using Three-Photon Microscopy of 5-Hydroxytryptamine Autofluorescence," *Biophys. J.* 76:1835-1846 (1999).

Williams et al., "Multiphoton Microscopy in Biological Research," *Curr. Opin. Chem. Biol.* 5:603-608 (2001).

Williams et al., "Three-Photon Excitation Imaging of Serotonin Secretion by RBL-2H3 Cells," *Biophys. J.* 72:A156 (1997) (Abstract).

Williams et al., "Two-Photon Molecular Excitation Provides Intrinsic 3-Dimensional Resolution for Laser-Based Microscopy and Microphotochemistry," *FASEB Journal* 8:804-813 (1994).

Xu et al., "Multiphoton Excitation Cross-Sections of Molecular Fluorophores," *Bioimaging* 4:198-207 (1996).

Xu et al., "Multiphoton Excitation of Fluorophores in Nonlinear Laser Microscopy," *OSA ILS-XII/Optics & Imaging in the Information Age* p. 158 (1996) (Abstract).

Xu et al., "Multiphoton Excitation of Molecular Fluorophores and Native Biological Absorbers," *Biophys. J.* 72:A90 (1997) (Abstract).

Xu et al., "Multiphoton Excitation of Molecular Fluorophores and Nonlinear Laser Microscopy," in J. Lakowicz, ed., *Topics in Fluorescence Spectroscopy*; vol. 5: *Nonlinear and Two-Photon-Induced Fluorescence*, New York: Plenum Press, pp. 471-540 (1997).

Xu et al., "Multiphoton Fluorescence Excitation: New Spectral Windows for Biological Nonlinear Microscopy," *Proc. Natl. Acad. Sci. USA* 93:10763-10768 (1996).

Xu et al., "Three-Photon Excited Fluorescence and Applications in Nonlinear Laser Scanning Microscopy," *Biophys. J.* 70:A429 (1996) (Abstract).

Zipfel et al., "Live Tissue Intrinsic Emission Microscopy Using Multiphoton-Excited Native Fluorescence and Second Harmonic Generation," *Proc. Natl. Acad. Sci. USA* 100(12):7075-7080 (2003).

Zonios et al., "Morphological Model of Human Colon Tissue Fluorescence," *IEEE Transactions on Biomedical Engineering* 43(2):113-122 (1996).

Supplementary Partial European Search Report for European Patent Application No. 04817749.7 (Aug. 3, 2009).

* cited by examiner

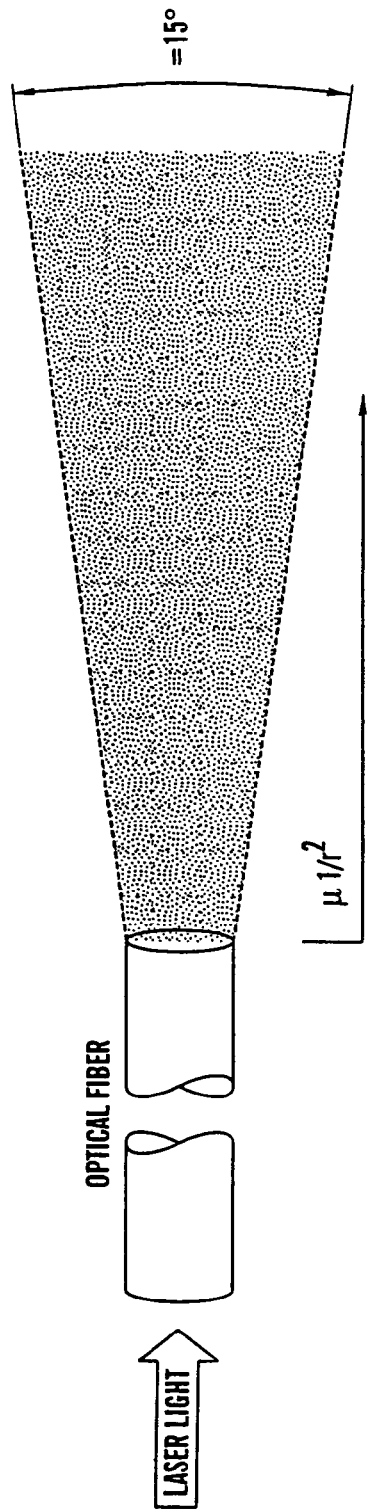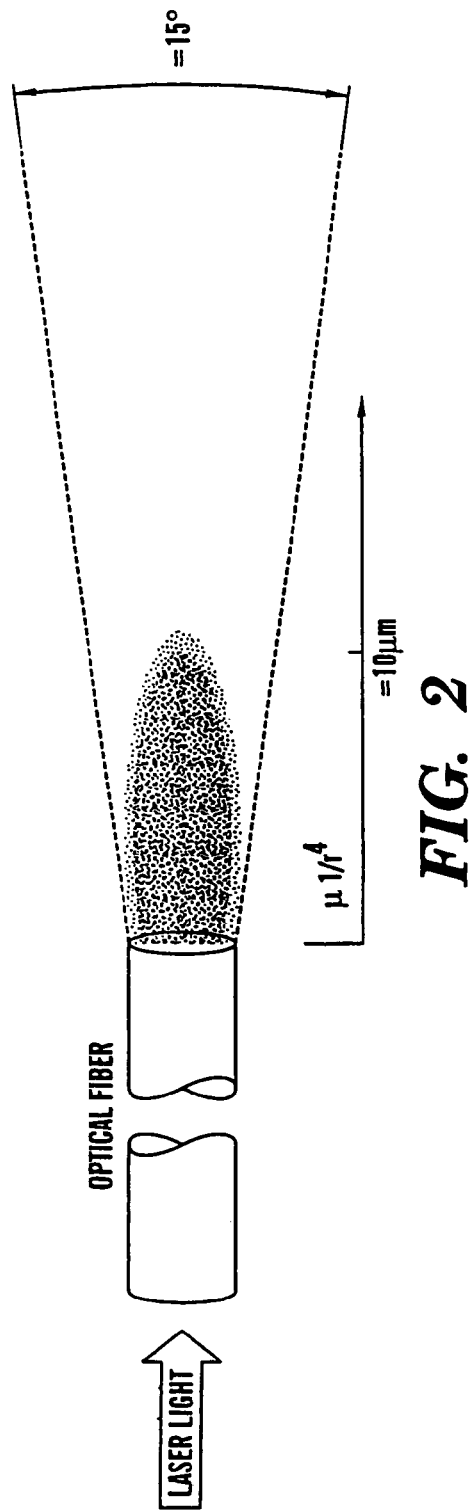

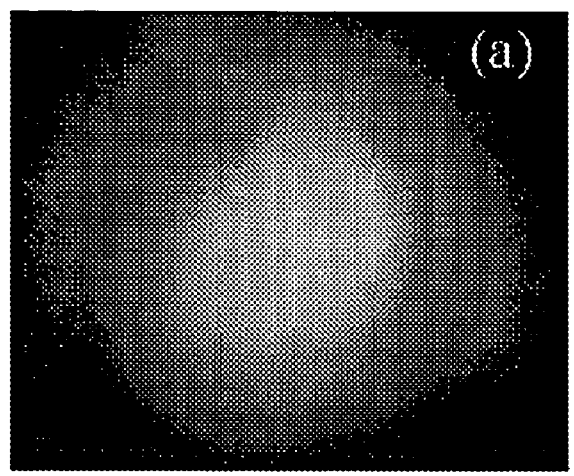
FIG. 8A
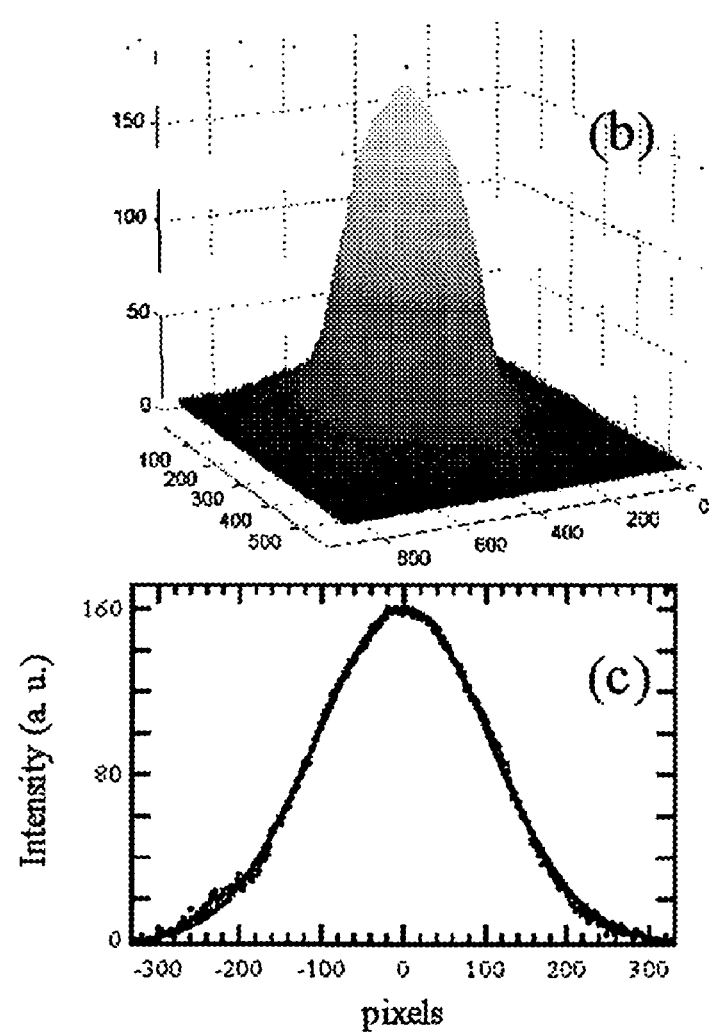
FIG. 8B
FIG. 8C ically, the NA is about 0.2 and the included cone angle is ~23° in air.) With single photon (i.e., linear) excitation this angular spreading is a problem, because equal total amounts of fluorescence are excited in every spherical section at each distance from the end of the fiber until attenuated by absorption and scattering. This effect is schematically illustrated in FIG. 1. Fluorescence excitation is similarly spread out. Scattering does not attenuate the fluorescence excitation but does distribute it even more broadly. Consequently, the volume observed is ill-defined with its practical limits depending also on blood distribution and light scattering. It should be noted that these problems tend to persist even if lenses focus the illumination and/or prisms and mirrors deflect the light for side viewing.

OPTICAL FIBER DELIVERY AND COLLECTION METHOD FOR BIOLOGICAL APPLICATIONS SUCH AS MULTIPHOTON MICROSCOPY, SPECTROSCOPY, AND ENDOSCOPY

This application claims the benefit of U.S. Provisional Patent Application Ser. No. 60/496,241, filed Aug. 19, 2003.

This invention was developed with government funding under U.S. Army Research Office Grant No. DAAD 19-01-10341, National Science Foundation Grant No. PHY-9987990; National Science Foundation Grant No. DBI-0080792, National Center for Research Resources—National Institutes of Health Grant No. 1-510-RR15831-01, National Institutes of Health Grant No. P41-2RR04224, and National Institutes of Health Grant No. R33CA094311-01. The U.S. Government may have certain rights in this invention.

FIELD OF THE INVENTION

The present invention relates to the use of multiphoton excitation in conjunction with optical biopsy needles, endoscopes, and microscopes.

BACKGROUND OF THE INVENTION

Many crucial biological functions are mediated or accomplished by biomolecules and tissue structures that are intrinsically fluorescent. As a result, there is an opportunity to diagnose and study important biological events by measuring and localizing the spectra and tissue fluorescence emission. To investigate in vivo internal processes and structures in large organisms, such as human beings and agricultural animals, an endoscopic procedure which penetrates body cavities or even solid tissue may be required.

Endoscopy video imaging in body cavities ordinarily utilizes back-scattered white light applied through the endoscope to form a low-resolution color image of the internal surfaces of these cavities. Physicians often use the changes in shapes and changes in local apparent color (which are often due to changes in blood distribution) to recognize disease states, such as malignant tumors or inflammation. Unfortunately, these clues are frequently not sufficient, especially for detection of the early onset of disease. Diagnostic improvements have been made by quantitative measurements of the light scattering and of tissue fluorescence emission.

Ordinarily, the light required to excite the fluorescence of tissue is delivered through an optical fiber or fiber bundle that is inserted through a small tube built into the endoscopic pipe. Small optical fibers or fiber bundles for emission collection can be passed through the same tube, and/or the delivery fiber can be used for epi-collection. Some of the strongest tissue fluorescence usually seen in this procedure is due to NADH (nicotinamide adenine dinucleotide), collagen and aromatic amino acids, such as tryptophan. Their fluorescence is excited by absorption of ultraviolet light of about 250 to 450 nm wavelength corresponding to photon energies of around 2 to 4 eV or sometimes slightly longer wavelength visible light may be used for intrinsic emitters such as flavoproteins. It is also possible to excite and collect fluorescence emissions from added fluorescent dyes such as fluorescein to increase contrast and signal strength.

A first problem is that this light is strongly absorbed by hemoglobin and oxyhemoglobin in the blood so that penetration of the illumination into the tissue depends on their concentration and distribution.

A second problem is that the illumination exiting the optical fibers into tissue fans out at an included angle determined by the numerical aperture (NA) of the optical fiber. Small lenses can be used so that the light first converges to a focus but it then fans out beyond the focal plane. (Typ- Femtosecond-pulse propagation through large-core microstructured fibers was investigated. Although these fibers are highly multimode, excitation of the fundamental mode is readily achieved, and coupling to higher-order modes is weak even when the fiber is bent or twisted. For prechirped input pulses with energies as large as 3 nanojoule ("nJ"), pulses as short as 140 femtoseconds ("fs") were produced at the output of the fiber. Such a system could prove to be extremely useful for applications such as in vivo multiphoton microscopy and endoscopy that require delivery of femtosecond pulses and collection of fluorescence.

Femtosecond pulses generated in a diffraction-limited beam have become an important tool for many science and technology areas. For a number of applications, it is desirable to deliver these pulses via an optical fiber over a distance of a few meters to a specific location. It is commonly believed that one must use single-mode fibers ("SMFs") to ensure the high spatial quality of the beam as well as to avoid additional temporal broadening as a result of intermodal dispersion. However, as a result of the very small (<5 μm) core size of SMFs, self-phase modulation broadens the pulse spectrum for pulse energies as low as a few picojoules, and the dispersion-induced temporal broadening cannot be readily compensated for by means of prechirping.

For applications such as multiphoton microscopy (Williams et al., *Curr. Opin. Chem. Biol.* 5:603 (2001)), fiber delivery of femtosecond pulses could improve the existing microscope design and, more importantly, lead to the development of miniaturized instrumentation for both basic research in biology and clinical applications such as nonlinear endoscopy. To preserve the pulse width after propagation of the pulse through the fiber, one must compensate for or minimize dispersive and nonlinear effects. Fiber dispersion can be compensated for by imparting a suitable frequency chirp on the input pulses. Propagation of negatively chirped pulses in a SMF was investigated (Myaing et al., *Opt. Express* 7:210 (2000)), and the width of the output pulses was found to scale sublinearly with pulse energy, but even for a pulse energy of 0.5 nJ the output pulse width exceeded 0.5 ps. Atherton and Reed (Atherton et al., *Proc. SPIE* 3269:22 (1998)) used a single-grating precompensator to deliver 100-fs pulses with energies as great as 0.7 nJ through a 3-m-long fiber. To minimize the nonlinearity, they stretched the pulse in the compensator by an amount that was more than the amount that was compensated for by the fiber, and an additional piece of positive dispersive glass was used to restore the pulse nearly to its initial duration. However, the use of the additional piece of glass after the fiber prevents this approach from being applicable in those cases when the fiber is intended to be used directly as a probe. An interesting scheme employing two fibers and six prisms was demonstrated (Clark et al., *Opt. Lett.* 26:1320 (2001)), in which both spectral and temporal compression were used to achieve output pulses with nearly the same duration as the input pulse. As a result of third-order dispersion, the output pulse was still distorted, but was significantly shorter than that delivered by application of a negative prechirp. An alternative approach to minimizing nonlinearity is to utilize a fiber with a larger core size and thus reduce the effective nonlinearity. However, for maintenance of a single transverse mode, the increase in core size must be accompanied by a decrease of the core-cladding refractive-index difference, which, in turn, results in a rapid increase of bend losses.

New possibilities for tailoring the optical properties of the guided modes are created with the use of recently developed microstructured fibers (MFs) (Birks et al., *Electron. Lett.* 31:1941 (1995) and Knight et al., *Science* 282:1476 (1998)). MFs can have a significantly larger effective core—cladding index difference than that of conventional fibers, and as observed (Ranka et al., *Opt. Lett.* 25:796 (2001)) with small core diameters, even under conditions in which the fiber is multimode, the fundamental mode can be robustly excited such that for all intents and purposes the fiber behaves as a SMF. Furthermore, the bend losses are minimal. However, it appears that there has not yet been an investigation of how large the core can become and yet still maintain this effective single-mode behavior. In addition, any such fiber must readily allow coupling from free space to the fundamental mode without significant sensitivity to input coupling conditions.

The present invention is directed to overcoming these deficiencies in the art.

SUMMARY OF THE INVENTION

One aspect of the present invention relates to a method of detecting disease within a particular tissue of a plant or animal. This method involves activating the particular plant or animal tissue by introducing at least one input pulse of radiation through at least one large-core microstructured multimode optical fiber under conditions effective to deliver at least one output pulse of radiation from the fiber to promote a simultaneous nonlinear or multiphoton activation of the particular plant or animal tissue. As used herein, the term "nonlinear activation" means any nonlinear multiphoton absorption process which may or may not lead to fluorescence, as well as any nonlinear scattering process such as second harmonic generation. As used herein, the term "nonlinear signal" means (1) fluorescence produced from a nonlinear multiphoton absorption process, (2) nonlinear scattering, and/or (3) non-fluorescence signals produced from a nonlinear multiphoton absorption process. Collection of second harmonic ("SH") light in the backward direction is possible with certain structures such as collagen which can directly generate backward propagating SH (Zipfel et al., *PNAS* 100(12):7075 (2003), which is hereby incorporated by reference in its entirety). Forward directed SH can also be (linearly) backscattered by the tissue and collected by the collection fiber(s). The signals (fluorescence and/or nonlinear scattering) generated are collected back through the delivery fiber and/or through auxiliary collection fibers, and then compared to signals emitted by exciting healthy tissue of the particular plant or animal, with any differences indicating the possibility of disease. The at least one large-core microstructured multimode optical fiber has a numerical aperture of equal to or greater than about 0.2.

Another aspect of the present invention involves a method of producing an image of an internal region of a particular tissue within a plant or animal. This method involves activating the particular plant or animal tissue by introducing at least one input pulse of radiation through at least one large-core microstructured multimode optical fiber under conditions effective to deliver at least one output pulse of radiation from the fiber to promote a simultaneous multiphoton activation and/or nonlinear activation of the internal region of the particular tissue within the plant or animal and produce intrinsic fluorescence, fluorescence from added contrast-enhancing fluorophores, non-fluorescence signals produced from non-linear multiphoton absorption processes, and/or nonlinear scattering signals. By scanning the activating radiation delivered by the fiber and temporally correlating the signal produced with the illumination position, a raster-scanned image can be created.

The present invention also relates to a method of detecting and localizing fluorescence or other nonlinear signals within a subject. This method involves applying radiation to an internal surface of the subject through at least one large-core microstructured multimode optical fiber. Each fiber has a numerical aperture of equal to or greater than about 0.2 and terminates in a tip proximate to the internal surface. Radiation is applied under conditions effective to cause simultaneous nonlinear activation of molecules within the internal surface and, as a result, nonlinear signals are produced proximate to the tip of the at least one large-core microstructured multimode optical fiber. Application of the radiation to the internal surface involves introducing at least one input pulse of radiation through at least one large-core microstructured multimode optical fiber under conditions effective to deliver at least one output pulse of radiation.

Another embodiment of the present invention relates to a method of detecting and localizing nonlinear signals within a body of penetrable material. This method involves applying radiation to an internal region of the body of penetrable material through at least one large-core microstructured multimode optical fiber. Each fiber has a numerical aperture of equal to or greater than about 0.2 and terminates in a tip proximate to the internal region. In one embodiment, radiation is applied under conditions effective to cause simultaneous multiphoton absorption of fluorophore molecules within the internal region and, as a result, fluorescence is excited proximate to the tip of the at least one large-core microstructured multimode optical fiber. Application of the radiation the internal region involves introducing at least one input pulse of radiation through at least one large-core microstructured multimode optical fiber under conditions effective to deliver at least one output pulse of radiation.

The present invention utilizes multiphoton absorption to cause nonlinear signals, excite intrinsic fluorescence of tissue and/or added fluorophores with good spatial resolution in order to recognize disease by nonlinear spectroscopy. The most useful intrinsic tissue fluorescence for this purpose is most likely to require absorption of ultraviolet energies for excitation. Multiphoton excitation provides the added convenience of infrared illumination to provide the necessary excitation energy by simultaneous absorption of two or more photons by the fluorescent molecules or structures.

The present invention also utilizes multiphoton illumination to generate nonlinear scattering signals such as second harmonic generation with good spatial resolution in order to recognize disease by nonlinear spectroscopy.

The same advantages described above for internal multiphoton nonlinear spectroscopy through optical fibers penetrating a body cavity or tissue can be advantageously applied to probe other penetrable materials that are, or can be made, fluorescent, or those that generate nonlinear scattering signals or other nonlinear signals. Some examples of such other uses include probing materials such as food products, natural or manmade polymeric structures (e.g., collagen gels or scaffolding), or porous media, and rapid in vitro screening applications utilizing fluorescence. The methods of the present invention may also be coupled with high-throughput assays to identify potential drug candidates. The penetrable body of material may include non-liquid and liquid samples. The advantage in the latter example is that multiphoton illumination allows for efficient simultaneous excitation of different fluorophores using IR light (Xu et al., *PNAS* 93(20): 10763, (1996), which is hereby incorporated by reference in its entirety), eliminating the need for multiple excitation sources. Furthermore, the high NA (typically>0.6) of the microstructured fibers would allow for much more efficient collection of signal back through the fiber than possible with a conventional single mode fiber (NA<0.2) since collection scales with the fourth power of the NA (i.e., $NA^2$).

One important advantage of multiphoton excitation is that the illumination is not strongly absorbed by hemoglobin and myoglobin and, in fact, not strongly absorbed by any other common tissue components. Linear scattering of infrared light by tissue is also significantly less than scattering by ultraviolet wavelengths. The principal advantage of multiphoton excitation, however, for endoscopic fluorescence and nonlinear scattering spectroscopy is that the effective focal volume within which the sample is activated is well defined and highly localized (FIG. 2). The reason for this is that the rate of two-photon excitation of fluorescence or for generation of second harmonic signals is proportional to the square of the illumination intensity. For higher multiphoton processes, the power law exponent of the intensity is larger, cubic for three-photon excitation for example. In multiphoton laser scanning microscopy, this higher power law feature makes possible three-dimensional resolution without generating out-of-focus fluorescence that would have to be excluded by confocal spatial filtering.

The same illumination conditions are also suitable for generation of second and third harmonic generation in certain suitable tissues. The second and third harmonics are generated, respectively, at exactly one half and one third of the laser illumination wavelengths and can be used with the intrinsic fluorescence to help characterize the tissue.

An analogous advantage applies to fluorescence multiphoton excited by laser light transmitted through an optical fiber as in application to endoscopic tissue fluorescence. Although the illumination intensity fans out just as for one-photon excitation with roughly equal total power at each value of radius from the end of the fiber or focal plane of any focusing lens, the excited fluorescence does not follow this fanned out illumination. In the case of two-photon excitation through a single mode optical fiber, the distribution of fluorescence is localized near the fiber tip in a shape resembling a candle flame beginning at the fiber tip. This effective focal volume is defined by the spatial distribution of the square of the illumination intensity for two-photon excitation. The square of the illumination intensity falls off roughly as the reciprocal fourth power of the distance from the fiber tip so that the fluorescence excitation is localized. Significant fluorescence is emitted only from this limited volume where the square of the excitation intensity is large, as illustrated in FIG. 3. Lenses, prisms, etc. can be used to shift the effective focal volume beyond the end of the optical fiber and/or to provide a side-looking orientation without losing the advantages of multiphoton excitation.

This effect provides a well-defined focal volume for the fluorescence excitation and allows useful spatial resolution which is sharp enough to resolve important anatomical structures. For example, in the colon, about 5 distinct layers should be distinguishable. At the surface of the endothelium, an array of crypts covers the area and is terminated in a cellular layer that closes the bottoms of the crypts, followed by several more layers including smooth muscle and connective tissue for a total of about 0.5 mm. These layers are readily resolved by multiphoton laser scanning microscopy exciting the intrinsic tissue fluorescence, which differs from layer to layer. Such layers and their perturbations by disease near the surface are thus distinguishable in the intact tissue by endoscopic spectroscopy of the tissue fluorescence with sufficient spatial resolution as provided by multiphoton excitation.

The multiphoton excitation of the present invention allows accurate spatial discrimination and permits quantification of fluorescence from small volumes whose locations are defined in three dimensions. This is especially important in cases where thicker layers of cells are to be studied. In this case, the fiber can penetrate the tissue to observe and resolve the multiphoton excited fluorescence of deeper layers, thus providing optical biopsy in situ. Furthermore, multiphoton excitation greatly reduces the background fluorescence and scattering artifacts.

The present invention incorporates a scheme that allows for simultaneous delivery of high-power sub-picosecond laser pulses and for collection of the generated fluorescence through the same large-core, high numerical aperture, microstructured optical fiber. Although these fibers are multimode, they are able to effectively propagate the pulses primarily in the single fundamental mode. Using only simple dispersion compensation at the input of the system, the large area of the fiber results in a small effective nonlinearity which allows for delivery of high peak-power laser pulses such that at the output of the fiber the pulse duration is approximately equal to that of the input pulse into the system. The high numerical aperture of the fiber permits efficient collection of fluorescence that is produced as a result of excitation at the output of the system by the sub-picosecond laser pulse. Such a system can effectively operate with input pulses over a large wavelength range spanning the visible and infrared regimes. The relatively large core-cladding index contrast also allows for the straightforward coupling of the input pulses from the laser source into the fundamental mode of the microstructured fiber. Such a system could prove to be extremely useful for applications such as in vivo multiphoton microscopy and endoscopy that require delivery of femtosecond pulses.

BRIEF DESCRIPTION OF THE DRAWINGS

FIG. 1 is a perspective drawing showing the spatial distribution of ultraviolet light emitted from a single mode optical fiber as well as the corresponding autofluorescence in accordance with the prior art. Here, the drop in intensity of radiation is reciprocal to the square of the distance from the tip of the optical fiber.

FIG. 2 is a perspective drawing showing the spatial distribution of ultraviolet light of two photon excitation fluorescence emitted from a single mode optical fiber in accordance with the present invention. Here, the pattern of illumination is nearly the same as for one-photon excitation. However, because the rate of two photon excitation is proportional to the square of the pulsed illumination intensity, the fluorescence intensity decreases from the tip of the fiber approximately as the reciprocal fourth power of the distance from the tip of the fiber providing a highly localized effective focal volume for excitation of the fluorescence. For higher order fluorescence excitation, the power law concentration of the emission is even stronger, reciprocal sixth power for three-photon excitation for example, although the sharpness of the effective focal volume could be reduced if a larger diameter optical fiber is used.

FIGS. 8A-8C show a beam profile at the output of the microstructured fiber MF1: digital camera photograph (FIG. 8A); intensity distribution (FIG. 8B); Gaussian fit of a cross section (FIG. 8C).

DETAILED DESCRIPTION OF THE INVENTION

Figure 3:
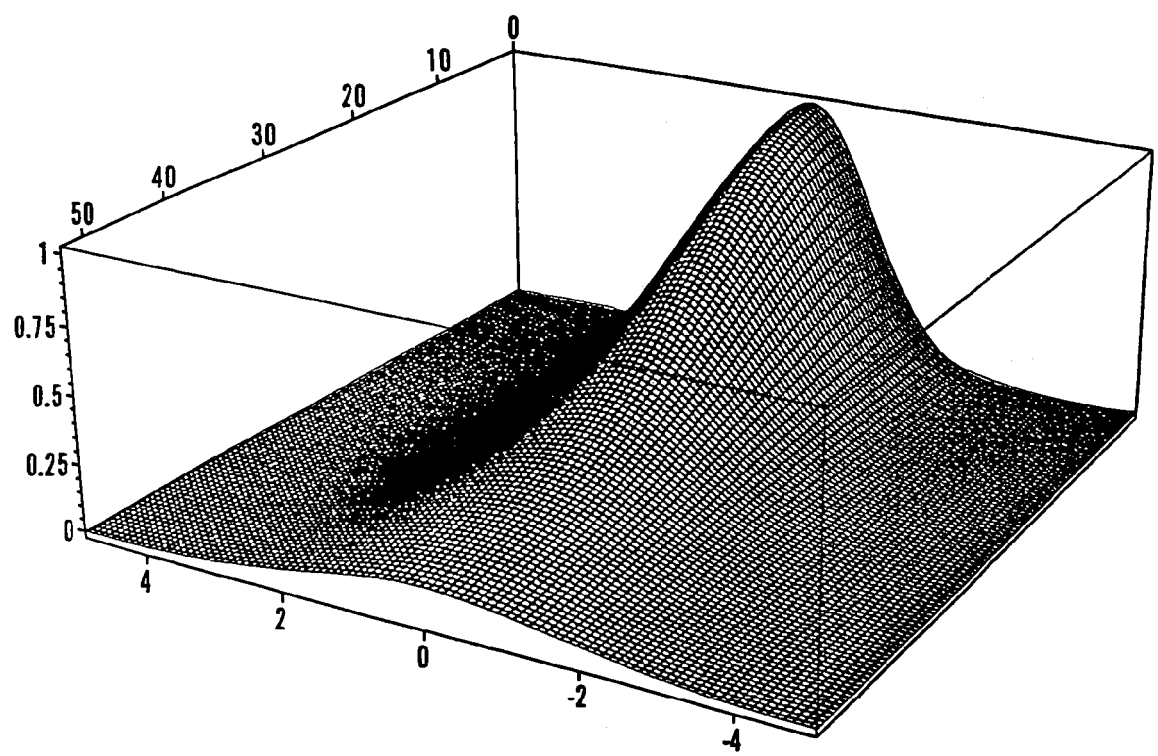
FIG. 3 shows a two photon excitation profile at the fiber output in the form of a Gaussian Intensity Profile. This figure is a representation of the spatial distribution of the two-photon excited fluorescence emission from a uniform fluorophore shown for a plane along the axis of the optical fiber beginning at the exit from the fiber. For the microstructured fibers used, the normalized maximum drops by half in about 50 micrometers along the axis and has a half maximum half-width of about 10 μm at the exit of this typical single mode fiber without any additional focusing optics.

One aspect of the present invention relates to a method of detecting disease within a particular tissue of a plant or animal. This method involves activating the particular plant or animal tissue by introducing at least one input pulse of radiation through at least one large-core microstructured multimode optical fiber under conditions effective to deliver at least one output pulse of radiation and to promote a simultaneous multiphoton excitation of the particular plant or animal tissue and to emit intrinsic tissue fluorescence, fluorescence from added contrast-enhancing fluorophores or fluorescent drugs and/or nonlinear scattering signals such as second harmonic. These signals are then compared to signals emitted by exciting healthy tissue of the particular plant or animal under the same conditions used to carry out the activating step. The particular tissue of a plant or animal where the signals differ from the signals emitted by activating healthy tissue of the particular plant or animal under the same conditions is identified as potentially diseased. The at least one large core microstructured multimode optical fiber has a numerical aperture of equal to or greater than 0.2.

As used herein to describe a characteristic of a large-core microstructured multimode optical fiber, the term "numerical aperture" ("NA") is defined as the sine value of the acceptance angle ("$\theta_a$") of the fiber, which is the half-conical-angle, as illustrated by the following formula:

$$NA = \sin\theta_a = (n_1^2 - n_2^2)^{1/2},$$

where $n_1$ and $n_2$ are the effective refractive indices of the core and the cladding, respectively. Another aspect of the present invention involves a method of producing an image of an internal region of a particular tissue within a plant or animal. This method involves activating the particular plant or animal tissue by introducing at least one input pulse of radiation through at least one large-core microstructured multimode optical fiber under conditions effective to deliver at least one output pulse of radiation from the fiber to promote a simultaneous multiphoton activation of the internal region of the particular tissue within the plant or animal and produce intrinsic fluorescence, fluorescence from added contrast-enhancing fluorophores and/or nonlinear scattering signals. By scanning the activating radiation delivered by the fiber and temporally correlating the signal produced with the illumination position, a raster-scanned image can be created. The at least one large-core microstructured multimode optical fiber has a numerical aperture of equal to or greater than 0.2. The at least one input pulse of radiation may be pulsed at a pulse duration of between about 10 and about 1,000 femtoseconds.

The present invention also relates to a method of detecting and localizing fluorescence within a subject. This method involves applying radiation to an internal surface of the subject through at least one large-core microstructured multimode optical fiber. Each fiber has a numerical aperture of equal to or greater than 0.2 and terminates in a tip proximate to the internal surface. Radiation is applied under conditions effective to cause simultaneous multiphoton absorption of fluorophore molecules within the internal surface and, as a result, fluorescent excitation proximate to the tip of the at least one large-core microstructured multimode optical fiber. Application of the radiation to the internal surface involves introducing at least one input pulse of radiation through at least one large-core microstructured multimode optical fiber under conditions effective to deliver at least one output pulse of radiation. The at least one input pulse of radiation may be pulsed at a pulse duration of between about 10 and about 1,000 femtoseconds.

Another embodiment of the present invention relates to a method of detecting and localizing fluorescence within a body of penetrable material. This method involves applying radiation to an internal region of the body of penetrable material through at least one large-core microstructured multimode optical fiber. Each fiber has a numerical aperture of equal to or greater than 0.2 and terminates in a tip proximate to the internal region. Radiation is applied under conditions effective to cause nonlinear activation of molecules within the body of penetrable material. In one particular embodiment, radiation is applied under conditions effective to cause simultaneous multiphoton absorption of fluorophore molecules within the internal region and, as a result, fluorescent excitation proximate to the tip of the at least one large-core microstructured multimode optical fiber. Application of the radiation to the internal region involves introducing at least one input pulse of radiation through at least one large-core microstructured multimode optical fiber under conditions effective to deliver at least one output pulse of radiation. The at least one input pulse of radiation may be pulsed at a pulse duration of between about 10 and about 1,000 femtoseconds.

Figure 4:
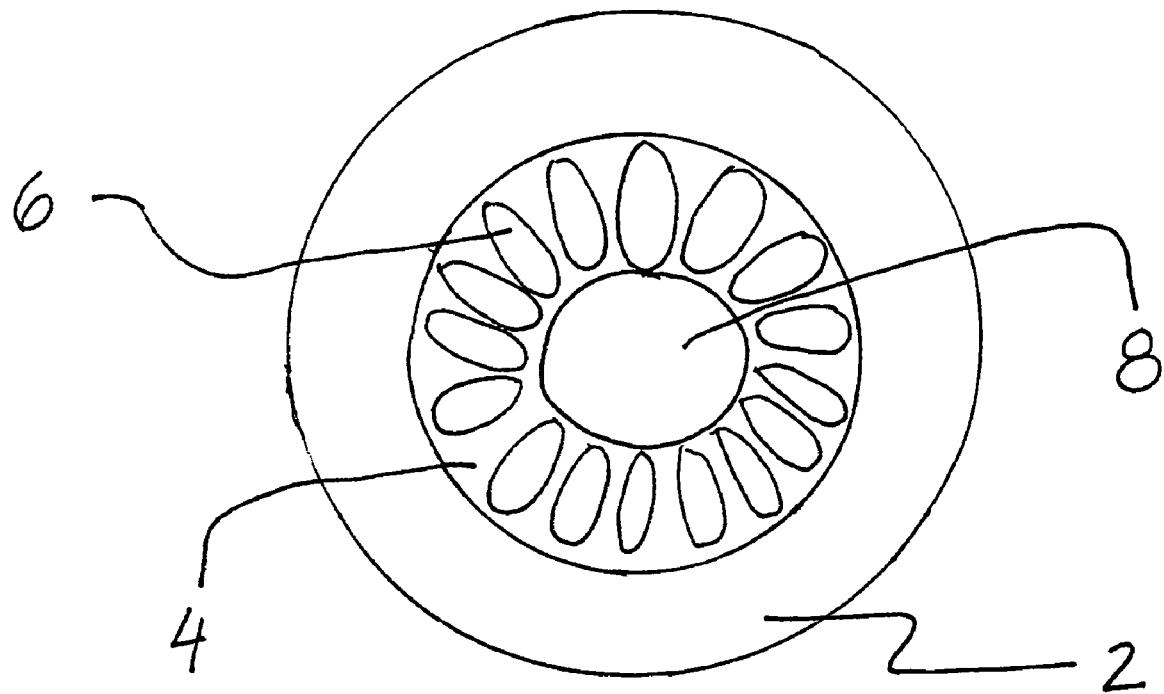
FIG. 4 is a schematic showing a cross-sectional view of an example of a large-core microstructured multimode optical fiber for use in the methods of the present invention.
Figure 5:
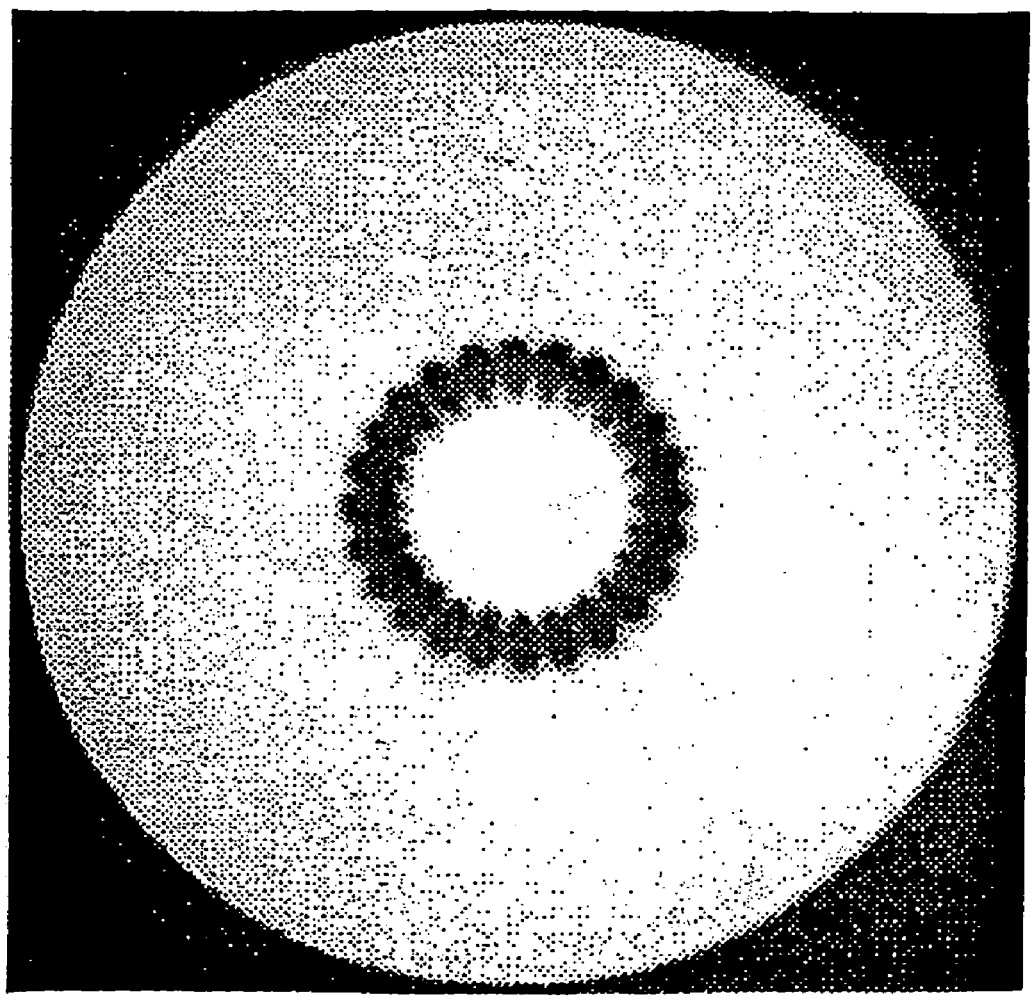
FIG. 5 shows cross-sectional views of an example of a large-core microstructured multimode optical fiber (commercially available from Crystal Fibre A/S, Denmark) for use in the methods of the present invention.

Cross-sectional views of examples of large-core microstructured multimode optical fibers suitable for use in the methods of the present invention are shown in FIGS. 4 and 5.

In particular, FIG. 4 shows core 8, air holes 6, glass webbing 4 (between air holes 6) that supports core 8, and outer cladding 2. Outer cladding 2, glass webbing 4, and core 8 are glass, while air holes 6 are air. The effective cladding index $n_2$ for this fiber would be $n_2^2 \sim f+(1-f)n_{glass}^2$, where f is the air-filling fraction of the regions (glass webbing 4 and air holes 6) surrounding core 8. FIG. 5 shows an image of the end of one particular embodiment of such a microstructured fiber.

One form of the present invention involves the use of multiphoton nonlinear endoscopic spectroscopy of tissue surfaces inside the cavities of living organisms. Endoscopic inspection and imaging at low resolution of the internal surfaces of body cavities is already a well-established standard medical procedure. Multiphoton endoscopic autofluorescence spectroscopy through optical fibers allows resolution of surface autofluorescence separately from the autofluorescence of underlying layers of the tissue. There are potentially numerous future improvements. Already it is possible to steer, point, and focus optical fibers with control apparatus to detect the fluorescence of tissue regions of interest in the endoscopy of body cavities. Analogous techniques are applicable to achieve the advantages of multiphoton fluorescent excitation for endoscopy. It can be anticipated that scanning of fibers or successive illumination of individual fibers or clusters in a bundle can be used to form multiphoton intrinsic fluorescence images. This aspect of the present invention can be used to image the fluorescence of tissues in internal channels such as the mouth, colon, esophagus, stomach, intestine, bladder, uterus, vagina, lung, ovaries, and throat. As a result, malignancy can be detected by recognition of differences in the fluorescence excited with ultraviolet excitation energies.

Figure 6A:
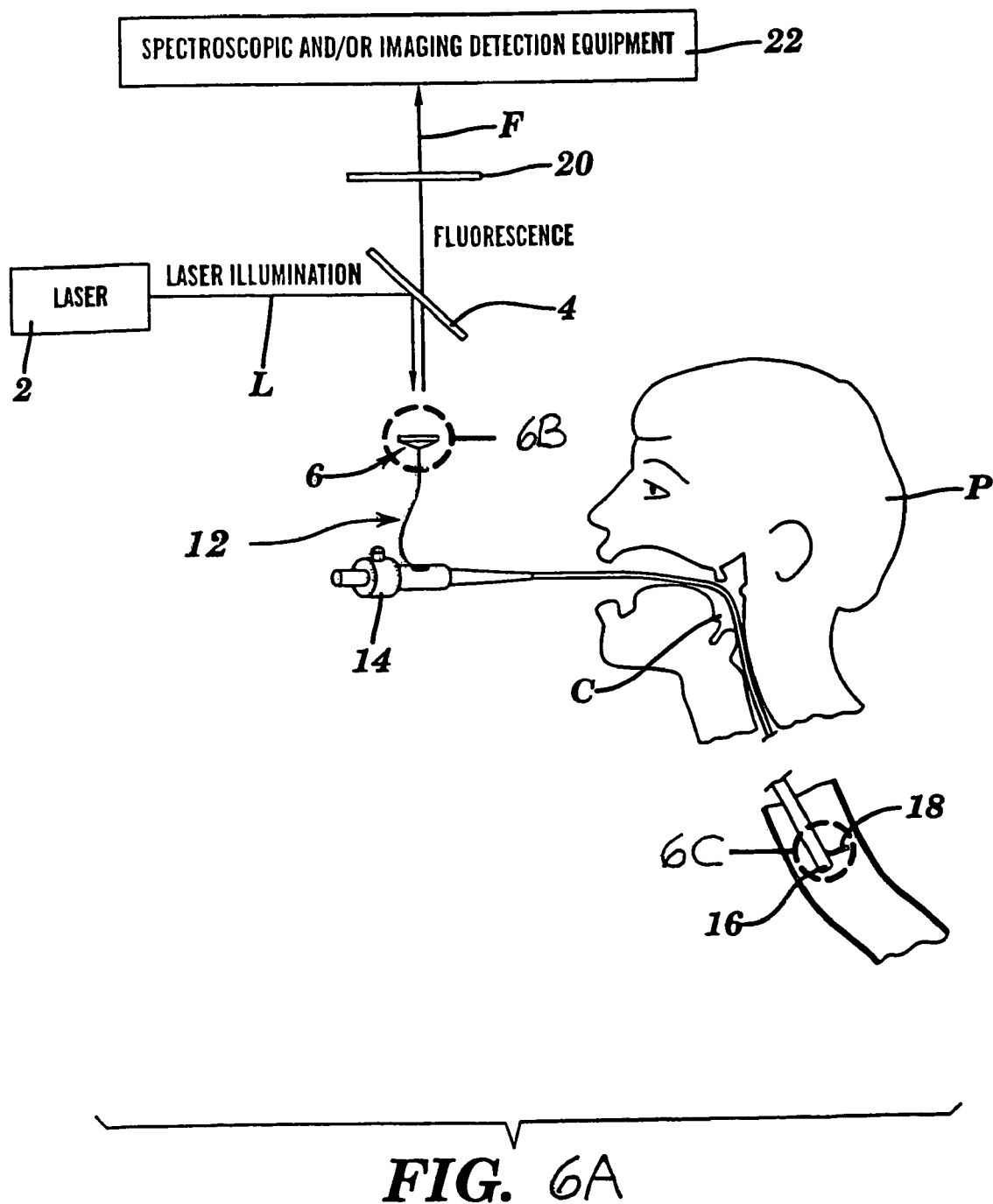
FIGS. 6A-6C show an endoscope arrangement in accordance with the present invention.
Figure 6B:
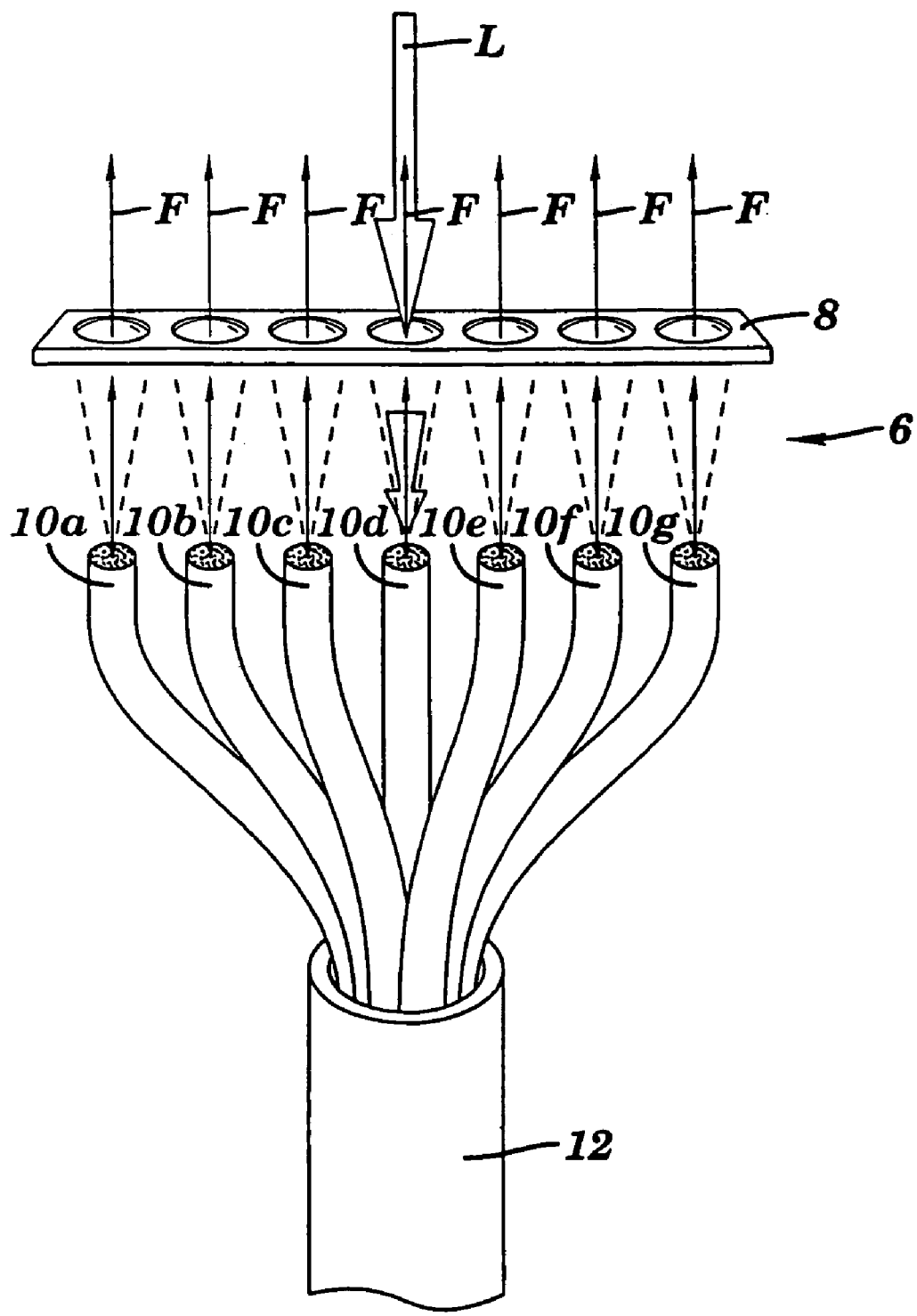
Figure 6C:
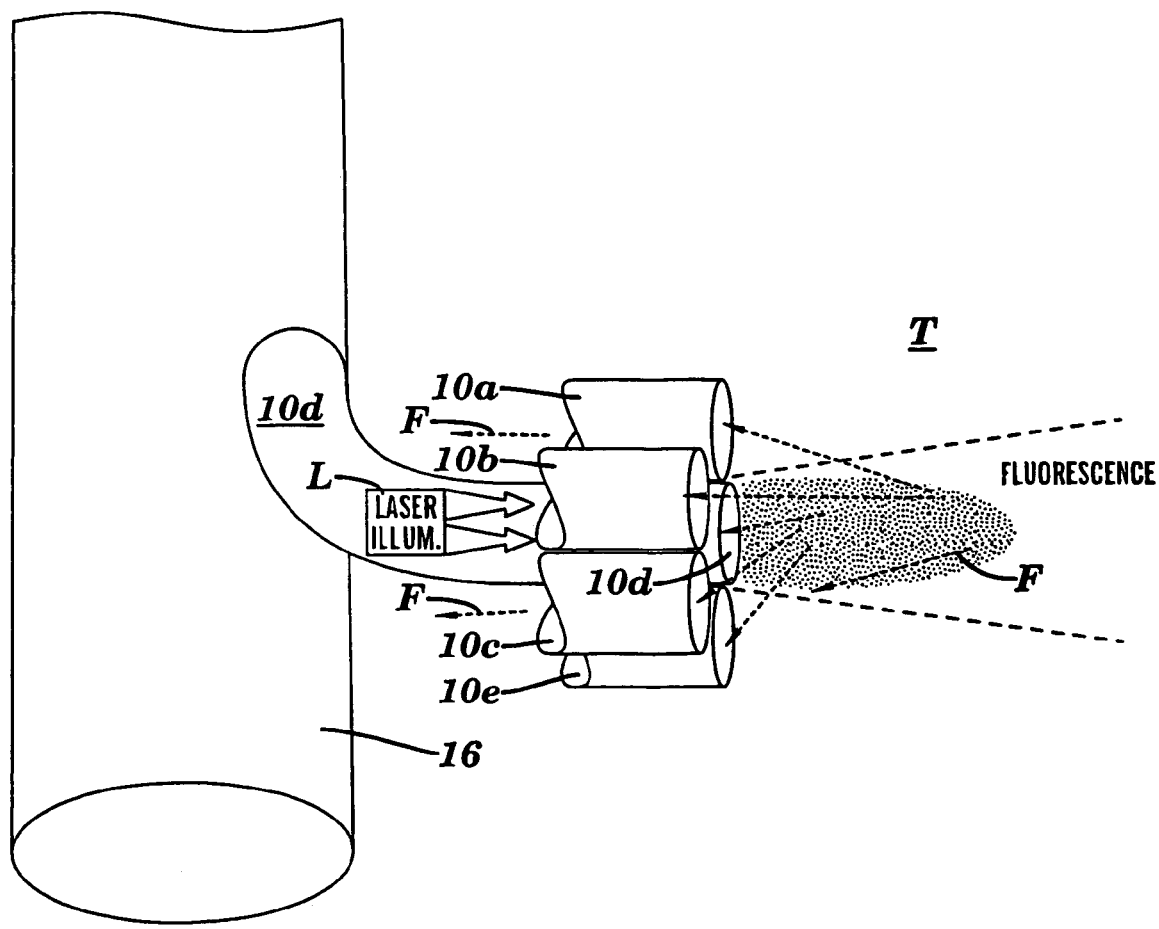

FIGS. 6A-6C show an endoscope arrangement in accordance with the present invention. In this embodiment of the present invention, laser 2 produces laser illumination L which is directed by dichroic filter 4 into optical fiber assembly 6. FIG. 6B shows optical fiber assembly 6 in more detail where laser illumination L passes through lens/focusing array 8 and into optical fiber 10d. Optical fibers 10a-10g are housed in cable 12 which is connected to endoscope head piece 14. The distal end of the endoscope is passed into the mouth of patient P through cavity C which, in this case, is the esophagus. The distal end of the endoscope terminates in endoscope tip 16 and excitation/collection unit 18. As shown in FIG. 6C, which shows excitation/collection unit 18 in more detail, laser illumination L passes through optical fiber 10d and is directed at tissue T. As a result, tissue T fluoresces at the tip of optical fiber 10d (see FIG. 2), and such fluorescence F is collected by optical fibers 10a-10g. The collected fluorescence F passes, in seriatim, through endoscope head piece 14, optical fiber assembly 6 (including lens/focusing array 8), dichroic filter 4, barrier filter 20, and into spectroscopic and/or imaging detection equipment 22.

Another form of the present invention is based on penetration of tissue itself with either at least one conventional optical fiber or with an optical biopsy needle. In this application, the optical fiber or optical biopsy needle is inserted in the tissue itself to sample the autofluorescence of the tissue at the end of the fiber or fibers. The fiber can function like a hypodermic syringe which can be inserted into the tissue as needed. Alternatively, the optical fiber's distal end can be configured to abut the surface of the plant or animal tissue being imaged. With multiphoton excitation, the volume at the end of the fiber where fluorescence is excited is well defined in principle. This can be carried out with a bundle of fibers wrapped around an initial fiber. Alternatively, a bundle of fibers which illuminate a larger volume can be utilized. In biopsy of dense tissue cancers, such as breast or liver cancer, the fiber can probe the fluorescence along insertion pathways.

Note that in contrast with conventional biopsy, which generally requires time consuming tissue fixing and staining procedures, the optical biopsy with multiphoton excited fluorescence spectroscopy provides immediate diagnostic spectral data as the probe is inserted and moved within the patient.

Figure 7A:
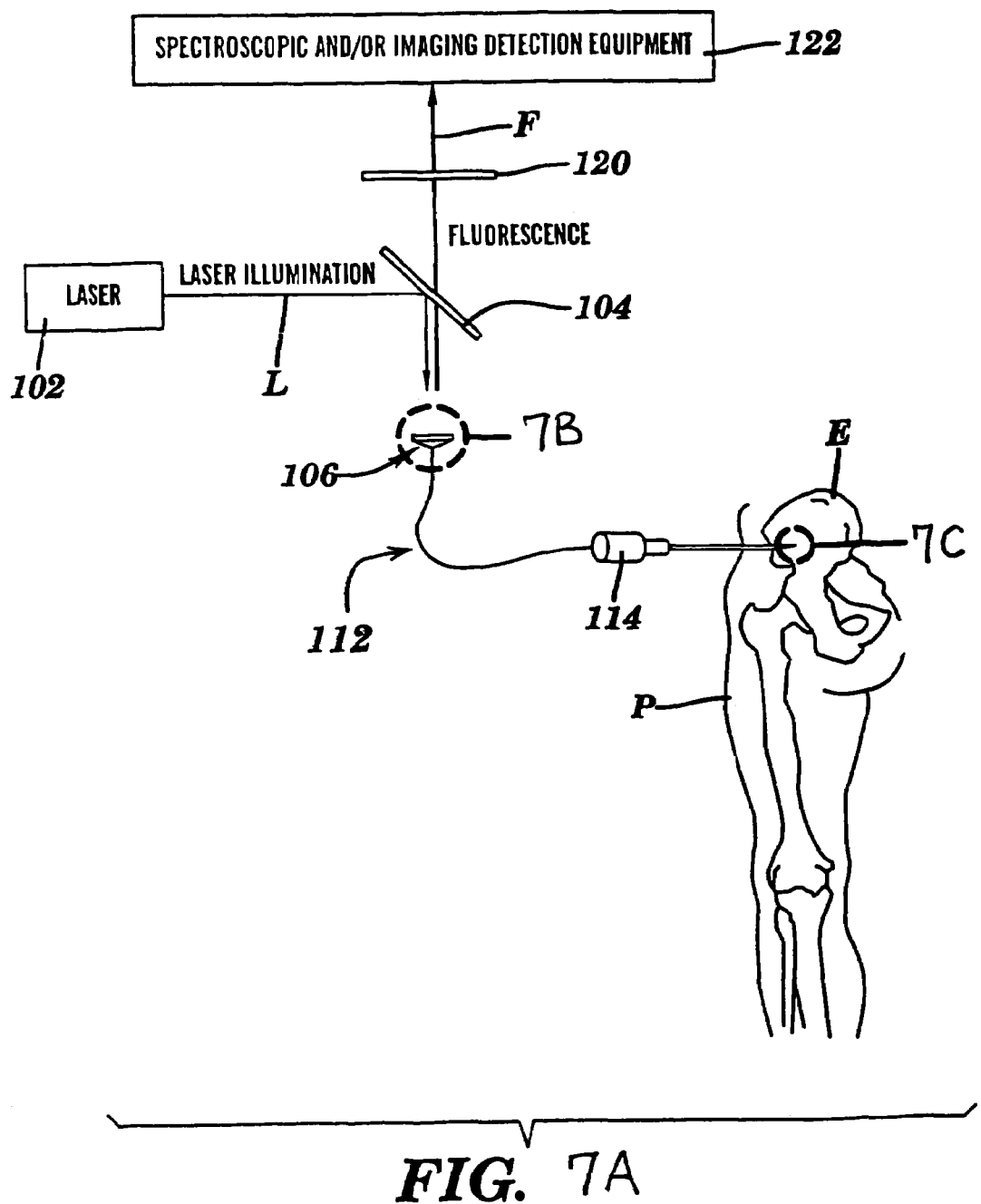
FIGS. 7A-7C show an optical biopsy needle arrangement in accordance with the present invention.
Figure 7B:
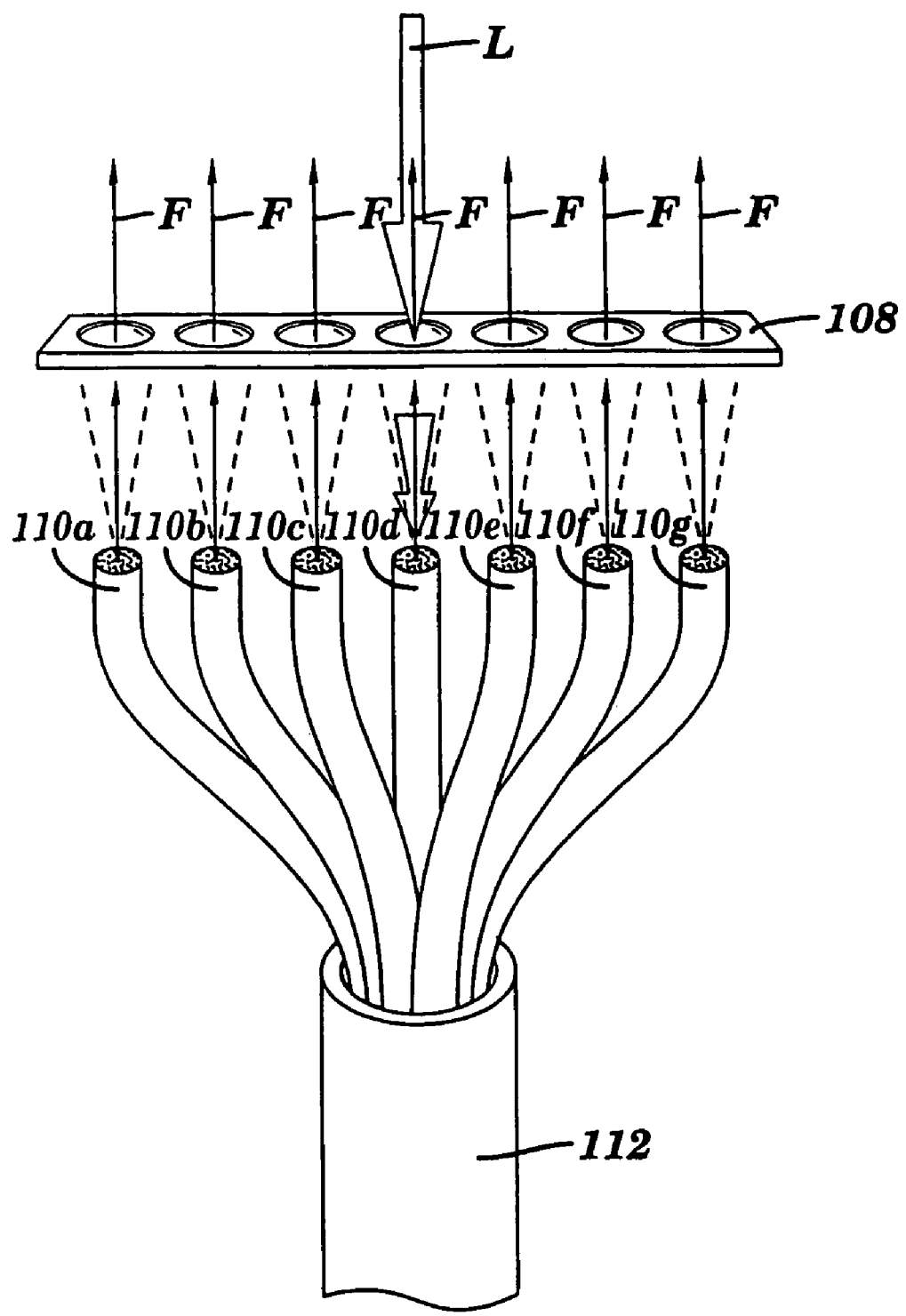
Figure 7C:
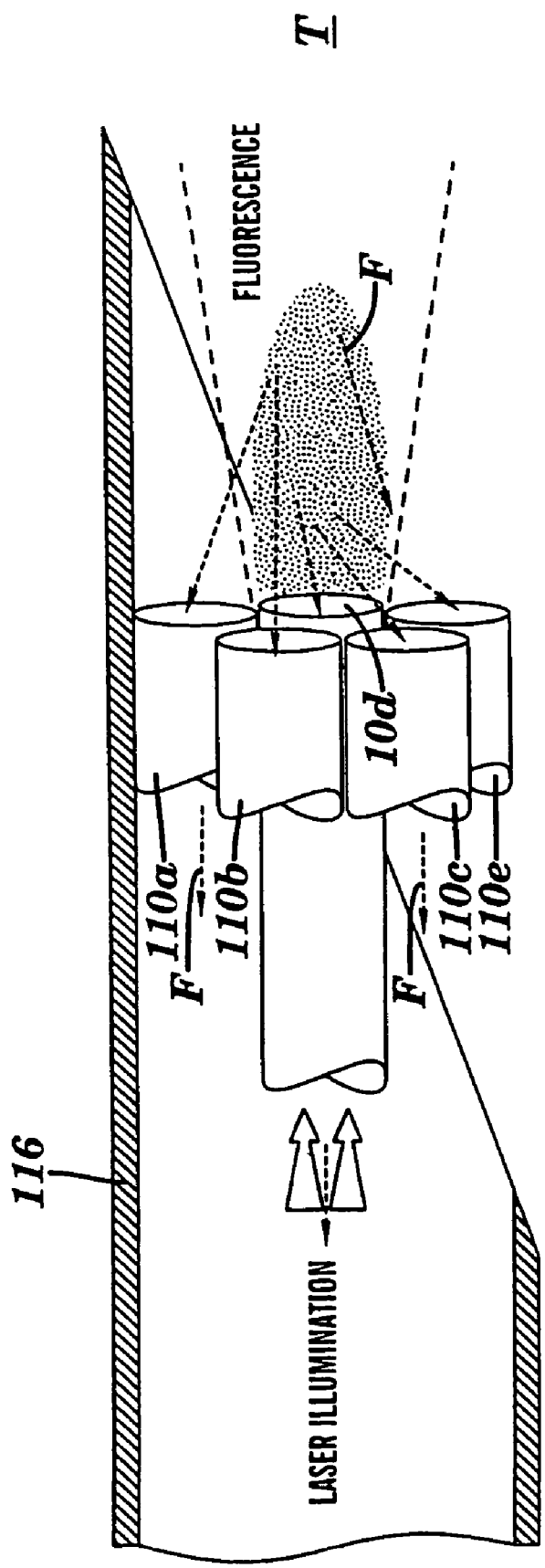

FIGS. 7A-7C show an optical biopsy needle arrangement in accordance with the present invention. In this embodiment of the present invention, laser 102 produces laser illumination L which is directed by dichroic filter 104 into optical fiber assembly 106. FIG. 7B shows optical fiber assembly 106 in more detail where laser illumination L passes through lens/focusing array 108 and into optical fiber 110d. Optical fibers 110a-110g are housed in cable 112 which is connected to optical biopsy needle head piece 114. The distal end of the optical biopsy needle (i.e. needle 116) is passed through the skin of patient P and into pelvis E. As shown in more detail in FIG. 7C, within needle 116, laser illumination L passes through optical fiber 10d and is directed at tissue T. As a result, tissue T fluoresces at the tip of optical fiber 10d (see FIG. 2), and such fluorescence F is collected by optical fibers 110a-110g. The collected fluorescence F passes, in seriatim, through optical biopsy needle head piece 114, optical fiber assembly 106 (including lens/focusing array 108), dichroic filter 104, barrier filter 120, and into spectroscopic and/or imaging detection equipment 122.

These forms of the present invention can also be carried out in combination where an endoscopic is inserted into a body cavity of a patient to provide a route for fibers to reach an internal surface of a body cavity from which the fibers can be inserted into the tissue to sample its successive layers. For example, in the search for the onset of cancer in the wall of the colon, the tissue has about 5 layers, each with its own characteristic optical properties and autofluorescence. Successive optical probing of each layer can distinguish them and recognize their changes by disease.

Detection of the multiphoton excited fluorescence and the second and third harmonic of the laser excitation generated in the tissue can be accomplished by endoscopy and optical biopsy through the optical fiber that provides the excitation and of course through surrounding fibers in a bundle or through thick optical tubes for efficient collection of light excited near the tip of the single mode excitation fiber or fibers. There is a significant advantage in fluorescence collection efficiency for multiphoton endoscopic tissue fluorescence over single photon excitation, because the emission is localized near the fiber tip where it is most accessible to collection optics. The same advantage applies in optical biopsy. The present invention can be carried out in several different ways including, without limitation: a non-imaging modality by delivery through a single microstructured optical fiber which may be surrounded by a plurality of collection fibers; low resolution imaging utilizing a plurality of optical delivery fibers, with or without an additional plurality of collection fibers; scanning of a single delivery fiber and collection of emissions by both the high NA delivery fiber (epi-collection) as well as a plurality of collection fibers; or scanning of the laser beam after it leaves the delivery fiber through an objective lens and collection back through the delivery fiber with or without an additional plurality of collection fibers.

Effective multiphoton molecular excitation is made possible, in accordance with the present invention, by the combination of (a) the very high, local, instantaneous intensity and (b) the temporal concentration of a pulsed laser. A high intensity, long wavelength, monochromatic light source which is focusable to the diffraction limit such as a titanium sapphire mode locked solid state laser, with each pulse having a duration of about 100 femtoseconds ($100 \times 10^{-15}$ seconds) at a repetition rate of about 80 MHz. Other lasers that are also effective for multiphoton excitation and harmonic generation can also be used. These ultrafast pulses are directed through the endoscope or optical biopsy needle to target tissue within a living plant or animal or, alternatively, a tissue specimen. Because of the high instantaneous power provided by the very short duration intense pulses focused to the diffraction limit, there is an appreciable probability that a fluorophore (a fluorescent dye), contained in the target, and normally excitable by a single high energy photon having a short wavelength, typically ultraviolet, will absorb two long wavelength photons from the laser source simultaneously. This absorption combines the energy of the two photons in the fluorophore molecule, thereby raising the fluorophore to its excited state. When the fluorophore returns to its normal state, it emits light, and this light then passes back through the endoscope or optical biopsy needle to a suitable detector.

The multiphoton excitation of fluorophores by highly intense, short pulses of light constitutes a general fluorescence microscopy technique for imaging which provides improved background discrimination and reduces photobleaching of the fluorophores. This is because the focused illumination provided in the microscope fills a converging cone as it passes into the specimen. All of the light which reaches the plane of focus at the apex of the converging cone, except the tiny fraction which is absorbed in the fluorophore, then passes out the opposite side of the specimen through a diverging cone. Only in the region of the focal point on the object plane at the waist formed by the converging and diverging cones is the intensity sufficiently high to produce multiphoton absorption in the specimen fluorophore, and this intensity dependence enables long wavelength excitation only in the small local volume of the specimen surrounding the focal point. This absorption is produced by means of a stream of fast, high intensity, femtosecond pulses of relatively long wavelength which retains a moderate average illumination intensity of long wavelength light throughout the remainder of the specimen outside the region of the focal point. As a result, photobleaching of the fluorophore outside the plane of focus is virtually eliminated. One-photon absorption of the long wavelength light is negligible, and outside the plane of focus the instantaneous intensity is too low for appreciable two-photon absorption and excitation, even though the time average illumination is in reality nearly uniform throughout the depth of the specimen. This effect also significantly reduces the damage to living cells.

In order to obtain three dimensional resolution, the present invention can utilize two-photon excitation of a fluorophore which has a one-photon absorption peak at a wavelength which overlaps or exceeds one-half that of the exciting light. For three-photon excitation, the one-photon absorption overlaps one-third that of the exciting light. To accomplish this, the laser produces a very short pulsed laser beam of high instantaneous power and of a relatively long wavelength, for example in the visible red or the infrared range. This light is directed to a specimen containing a fluorophore normally excited by a single photon having a short wavelength (e.g., ultraviolet radiation) range so that two low energy (red) photons must combine their energy to provide the same excitation of the specimen that would be provided by a single high energy (ultraviolet) photon. Both the excitation and hence the fluorescence rates in the specimen are proportional to the square of the intensity of the incident light. In the focused excitation laser beam, the intensity of the long wavelength incident light becomes high enough to excite the fluorophores in the specimen only in the region of the focal point. This focal point may be adjustably positioned within the specimen so that fluorescence and/or photolysis of the specimen are produced only in a selected ellipsoidal volume around the focus. Thus, in accordance with the present invention, only long wavelength excitation light has to pass through the specimen, and this long wavelength light is focused to produce sufficient intensity to excite fluorescence only in a very small region. This fluorescence is produced even if the fluorophore normally absorbs only in the ultraviolet. Since the focal point can be selectively positioned in the specimen, three-dimensional resolution is provided in both scanning fluorescence microscopy and in photolysis, including photolysis of photon-activatable reagents which can be released by photolysis.

In accordance with the present invention, the necessary excitation intensity is provided from a radiation light source which may be, for example, a titanium sapphire mode locked laser generating pulses of light having a wavelength in the red region of the spectrum, for example about 700-1000 nm, or with the pulses having a width of $10^{-9}$ seconds to $10^{-15}$ seconds, conveniently at about 80 MHz repetition rate. Other bright pulsed lasers may also be used to produce light at different relatively long wavelengths in the infrared or visible red region of the spectrum, for example, to generate the necessary excitation photon energies which will add up to the appropriate absorption energy band required by the fluorophores in the spectrum which normally would be excited by absorption of a single photon in the spectral region having wavelengths about one-half the wavelength of the incident light. If shorter excitation wavelengths are needed, the laser wavelengths can be divided by 2, 3, or 4 by external harmonic generation. Thus, for example, two photons in the visible red region at 750 nm would combine to excite a fluorophore which normally absorbs light in the ultraviolet region at or above 375 nm, while two photons in the infrared region of, for example, 1070 nm, would excite a fluorophore which absorbs at or above 535 nm in the visible light region.

In a modified form of the invention, the single wavelength light source can be replaced by two different long wavelength laser sources so that the incident light beam consists of two superimposed pulsed light beams of high instantaneous power and of different wavelengths. The wavelengths of the incident beam are selected to excite a fluorophore which is absorbent at a short wavelength which may be described as:

$$1/\lambda_{abs} = 1/\lambda_1 + 1/\lambda_2$$

where $\lambda_{abs}$ is the short wavelength of the absorber, and $\lambda_1$ and $\lambda_2$ are the laser incident beam wavelengths.

In two-photon excitation, with a typical two-photon cross section $\sigma_{2p}$ of $\sim 10^{-50}$ cm$^4$s, with the pulse parameters given above (100 fsec. pulses at a repetition rate of 80 MHz), and with the beam focused by a lens of numerical aperture NA of 1.4, the average incident laser power ($P_0$) of approximately 50 mW saturates the fluorescence output of a fluorophore at the limit of one absorbed photon per pulse per fluorophore. The number $n_a$ of photons absorbed per fluorophore per pulse depends on the following relationship (Denk et al., *Science*, 248:73 (1990), which is hereby incorporated by reference in its entirety):

$$n_a \sim P_o^2 \sigma_{2p} (\pi NA)^2 / \tau (hc\lambda f)^2$$

where:
  $\tau$ is the pulse duration;
  f is the repetition rate;
  $P_0$ is the average incident laser power;

δ is the photon absorption cross section;
h is 2π times Planck's constant;
c is the speed of light; and
NA is the numerical aperture of the focusing lens.

The fluorescence emission could be increased, however, by increasing the pulse repetition frequency up to the inverse fluorescence lifetime, which typically is:

$$\tau_f^{-1} = 10^9 s^{-1}$$

For comparison, one-photon fluorescence saturation occurs at incident powers of about 3 mW.

In addition to measurement of intrinsic tissue fluorescence with multiphoton excitation, it is possible to utilize the fluorescence of drugs to detect their location in tissue. Often, such drugs segregate to particular tissue structures or disease products, such as tumors. Multiphoton excitation can be used to identify them. Many important drugs absorb ultraviolet light to become fluorescent and are, therefore, effectively excited by multiphoton excitation. As a result, all of the advantages of multiphoton excitation of intrinsic tissue fluorescence together with the labeling features provided by the selective segregation or binding of fluorescence drugs are achieved. For example, the principal drug used to treat colitis, 5-amino salicylic acid, can be imaged in all of the layers of living colon tissue explants as the drug is metabolized. It can be located relative to complex tissue structure by imaging tissue autofluorescence due to collagen, nicotinamide adenine dinucleotide (NADH), and other structures. Multiphoton excitation of such drugs can be observed in vivo within tissues by multiphoton endoscopy and/or multiphoton optical biopsy.

Photoactive agents including fluorescent dyes are commonly used in multiphoton microscopy to image properties of cells and tissues. Suitable photoactive agents include dyes which are excited by multiphoton excitation such as, organic molecules whose fluorescence changes when they bind metal ions such as $Ca^{2+}$, $Mg^{2+}$, $Na^+$ or $K^+$ or $H^+$. Dyes which bind to the DNA double helix such as DAPI (4',6-diamidino-2-phenylindole, dihydrochloride) are particularly useful. Many such dyes are suitable for application in vivo.

Fluorescence distribution could be probed by multiphoton absorption endoscopic spectroscopy in living animals, including humans, to recognize inflammatory disease such as colitis and to follow the progress of its treatment. The distribution of fluorescent protoporphyrin IX, the metabolic product of aminolevulinic acid, which accumulates in cancer cells, would similarly be useful in cancer detection. NADH fluorescence may be the most promising cancer signal accessible by multiphoton absorption endoscopic spectroscopy, but it must be spatially localized by multiphoton absorption to distinguish it from collagen, which is similarly fluorescent in adjacent tissues. It has been known for many years that certain tissues and tissue components, particularly collagen, an important structural component of tissue that appears in many forms, are very effective at generating the second harmonic of bright coherent illumination. The second harmonic of illumination has exactly half of the wavelength and thus twice the photon energy of the fundamental illumination. Similarly, the third harmonic of illumination has exactly one third of the wavelength and, therefore, three times the photon energy. Generation of second harmonic radiation has, in fact, been demonstrated to be a useful phenomenon for microscopic imaging of cells. Because the illumination conditions required to excite second or third harmonic in complex tissue are nearly the same as for multiphoton fluorescence excitation, it is possible to take advantage of second or third harmonic generation, in tissues such as collagen, to complement multiphoton excitation of intrinsic tissue fluorescence. In complex tissues, the second or third harmonic radiation is frequently radiated through broad angles which makes it detectable along with the multiphoton excited fluorescence. The present invention can be used for a variety of purposes. For example, histological and clinical composition, structure, metabolic state, and vitality in the region of the subject can be determined. Alternatively, functional response to physiological and pharmacological stimuli and disease states can be detected in the region of the subject. Lastly, tissue or drug fluorescence excitation and emission spectra, luminosity, fluorescence lifetime, and temporal fluctuations in the region of the subject can be determined.

In addition, the described fiber delivery system would also be useful for delivery of femtosecond pulses into a conventional multiphoton microscope, allowing for ease of coupling of a mode-locked laser to the microscope system and relaxation in the placement of the femtosecond laser source. This implementation is different from those previously proposed (e.g., U.S. Pat. Nos. 5,995,281, 6,178,041, and 6,356,088, which are hereby incorporated by reference in their entirety), because all of the compensation is carried out before the fiber, rather than requiring dispersive glass after the fiber. Furthermore, much higher laser power is transmittable through the microstructured large core fibers than previously possible with an output pulse duration of approximately that of what entered the fiber. In one particular embodiment, the large-core microstructured multimode optical fiber is associated with a conventional multiphoton microscope under conditions effective to allow the at least one output pulse of radiation to be delivered to the conventional multiphoton microscope.

Various large-core microstructured multimode optical fibers can be used in the methods of the present invention. In one embodiment, the large-core microstructured multimode optical fiber can be a large core step-index fiber. As used herein, the term "large core step-index fiber" means an optical fiber having a large core/core-cladding step index contrast. A suitable example of a particular large core step index fiber for use in the present invention includes, without limitation, a silica rod in air. Other examples of large core step-index fibers suitable for use in the present invention include, without limitation, the MM-HMA-35 fiber (Crystal Fibre A/S, Denmark) and the MM-HMA-25 fiber (Crystal Fibre A/S, Denmark). In other embodiments, the large-core microstructured multimode optical fibers can be terminally associated with various devices known in the art to enhance focusing or imaging. For example, the large-core microstructured multimode optical fiber can be terminally associated with a focusing device. A suitable focusing device is one that is effective in decreasing the focal volume for delivering the output pulse of radiation from the fiber. Examples of suitable focusing devices include, without limitation, a lens or lens system. As another example, the large-core microstructured multimode optical fiber can be terminally associated with a scanning device under conditions effective to allow the scanning device to scan the nonlinear activation focal volume of the output pulse of radiation. This scanning device can be used to facilitate image formation using an image formation technique (e.g., laser scanning imaging) to form an image of the subject.

The present invention also relates to a device for coupling in radiation from an ultrashort mode-locked laser into the beam path of a microscope. The coupling in is effected by at least one large-core microstructured multimode fiber following the laser, where an optical arrangement is provided between the laser and the fiber that contains a device for dispersion compensation to add negative dispersion to the laser pulse. A suitable dispersion precompensator may include a multi-pass grating pair separated by a distance sufficient to produce the required negative dispersion, and/or any other device capable of producing enough negative dispersion to compensate for the dispersion caused by the core of the microstructured optical fiber. In one embodiment, the fiber coupling in is effected directly into a microscope to provide non-scanned nonlinear activation in the focal plane of the microscope. In another embodiment, the microscope is a laser scanning multiphoton microscope and the fiber delivers pulsed laser radiation through the scanning apparatus of the laser scanning microscope which is then delivered to the focal plane of the microscope to produce raster-scanned images. In another embodiment, the coupling in is effected via at least one large core microstructured mulitmode fiber.

EXAMPLES

Example 1

Delivery of Nanojoule Femtosecond Pulses Through Large-Core Microstructured Fibers This example reports on the delivery of femtosecond pulses through large-core MFs. 100-fs input pulses, which were negatively prechirped with a grating precompensator, were coupled into MFs with core diameters of 15 and 25 μM. The excitation of the fundamental mode was readily achieved, and only weak coupling to higher-order modes was observed even when the fibers were tightly bent. Under similar conditions, a standard SMF delivers pulses more than 10 times longer than those delivered by MFs.

The experiments involved the use of a standard SMF and two types of MF (commercially available from Crystal-Fiber A/S) (see FIG. 5). The parameters of the first MF (MF1) were core diameter, 15 μm; pitch, 11 μm; and hole diameter, 6.6 μm. The second MF (MF2) had a core diameter of 25 μm and an air-filling fraction of nearly unity. An SMF fiber designed for single-mode operation at 800 nm was also utilized. The lengths of the SMF and MF1 were 92 cm, whereas the piece of MF2 was 130 cm long. Unlike for small-core MFs (Ranka et al., *Opt. Lett.* 25:796 (2001), which is hereby incorporated by reference in its entirety), the zero-group-velocity wavelength for these MFs is essentially unshifted from that of the bulk silica.

The input 100-fs pulses centered at 800 nm were generated by a Ti:sapphire laser (Tsunami, Spectra-Physics) at a repetition rate of 80 MHz. The laser pulses were negatively frequency chirped by double passing through a pair of gratings (Treacy, *IEEE J. Quantum Electron.* QE-5:454 (1969), which is hereby incorporated by reference in its entirety) and were coupled into each of three fibers by focusing with either a 10× microscope objective (SMF and MF1) or a 4× objective (MF2). The coupling efficiency was approximately 50% for MF1 and 60% for MF2.

The temporal duration of the pulses was measured with an autocorrelator based on a two-photon detector (Ranka et al., *Opt. Lett.* 22:1334 (1997), which is hereby incorporated by reference in its entirety). For all fibers the distance between the gratings were adjusted to produce the shortest possible output pulses at an average power of 5 mW. Maintaining this fixed grating separation, the width of the output pulses were measured as a function of the power coupled into the fiber.

Figure 9A:
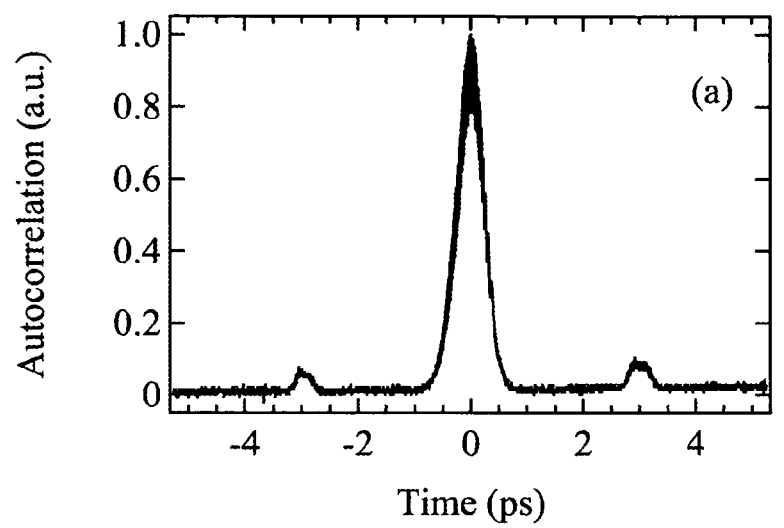
FIGS. 9A-9B show the intensity autocorrelation (FIG. 9A) and spectrum of an output pulse (FIG. 9B) for average power of 100 mW for MF1.
Figure 9B:
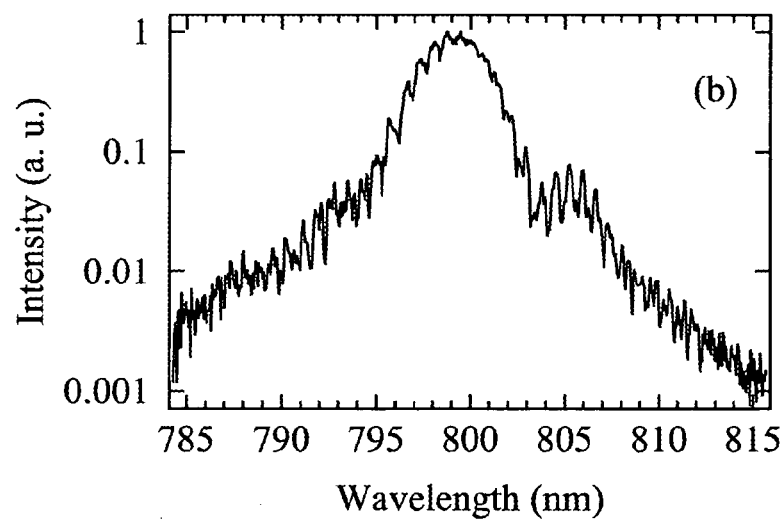

The parameters of the MFs indicate that they can support many transverse modes. Although its was observed that coupling into some of the higher-order modes occurred when the input coupling was misaligned, it was relatively straightforward to excite primarily the fundamental mode. A photograph of the output beam of MF1 and the intensity distribution are shown in FIGS. 8A-8C. A cross section of the intensity distribution is nearly perfectly fitted by a Gaussian function, which suggests that the excited mode is primarily the fundamental one. The last conclusion is supported by an intensity autocorrelation taken over a large distance (FIG. 9A). The central peak is 14 times as high as the side peaks, which is attributed to a higher-order mode. The delay between the two pulses allows one to determine the difference in the effective modal group indices to be $9.7 \times 10^{-4}$. This second, much weaker pulse creates a modulation of the output spectra (FIG. 9B). Moderate bending with bend radii as small as 1 cm or twisting of the fiber had no measurable effect on the output mode of MF1, and the spectrum exhibited little change. The fact that all peaks of the autocorrelation trace decrease indicates that the perturbation results in bend losses rather than in coupling to higher-order modes. In the case of MF2, bending caused the peak value of the autocorrelation signal to decrease slightly (less than 5%), as a result of coupling to higher-order modes. However, the slight change indicates that this coupling is weak and that the vast majority of the power is in the fundamental mode.

Figure 10:
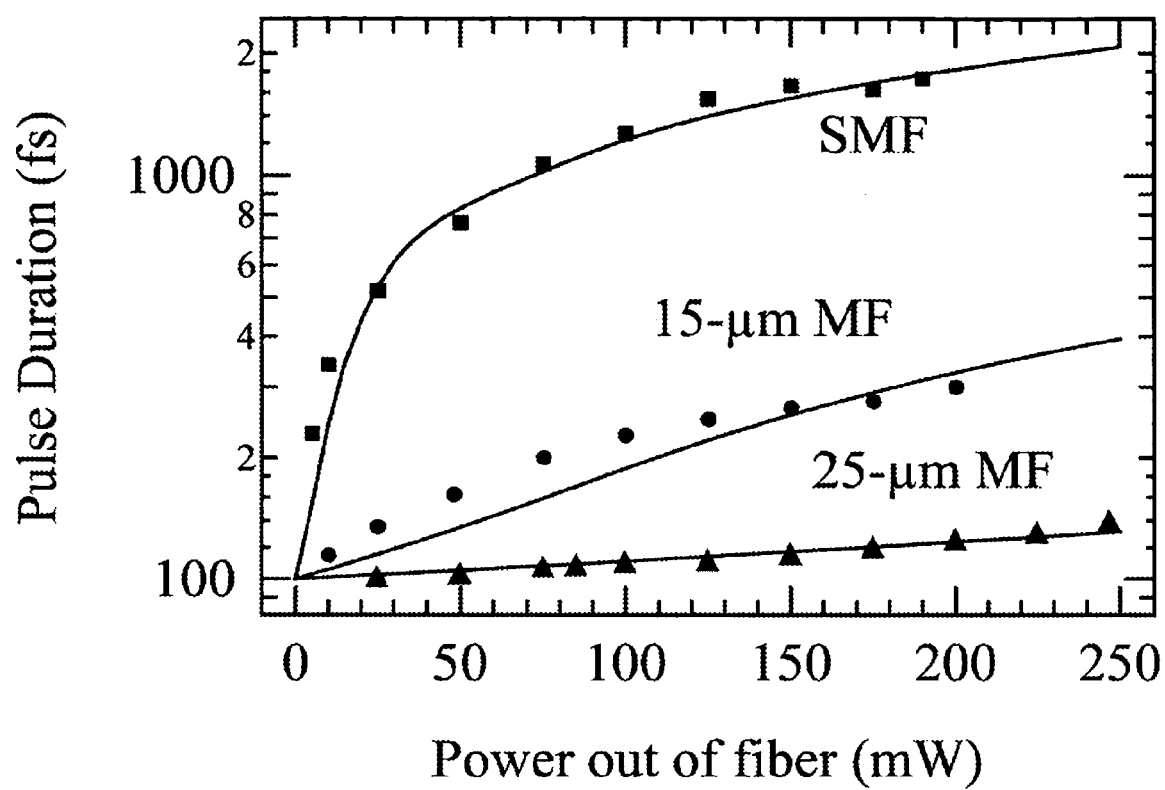
FIG. 10 shows the measured width of the output pulses as a function of power for SMF (squares), MF1 (circles), and MF2 (triangles) and theoretical results (solid curves) for all three fibers.
Figure 11:
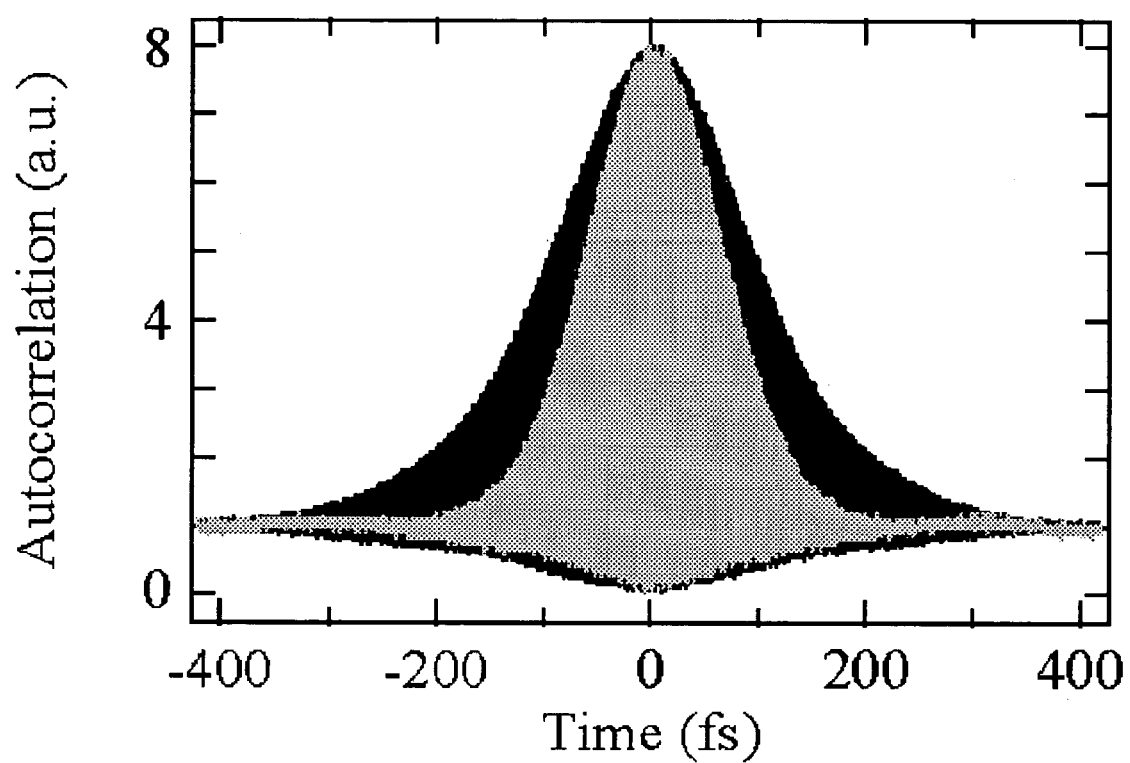
FIG. 11 shows the interferometric autocorrelation of the input pulse (gray) and the output pulse (black) from MF2 for a pulse energy of 3 nJ.

The measured dependence of the output pulse width on the coupled input power for SMF, MF1, and MF2 is shown in FIG. 10. As a result of the lack of compensation of the third-order dispersion by the two-grating compensator, even at low powers the output pulse remains slightly longer than the input one. Clearly, the MFs allow for delivery of much shorter pulses, especially at high powers. With MF1, output pulses as short as 300 fs for a pulse energy of 2.5 nJ were produced, which were approximately five times shorter than the output pulses with the same energy from a standard SMF. The larger core of MF2 allowed for the delivery of even shorter output pulses (FIG. 10) with durations as short as 140 fs for a pulse energy of 3 nJ (FIG. 11). The propagation of negatively prechirped pulses in the three types of fiber was simulated with the standard nonlinear Schrödinger equation model. As in the present experiments, the initial negative chirp was set to compensate for the linear dispersion at low power. The results are shown in FIG. 10 (solid curves). The best fit for each case was found by assuming that the beam radii in the fibers were 1.8, 6, and 14 μm for SMF, MF1, and MF2, respectively.

In conclusion, the potential of microstructured fibers for delivery of femtosecond pulses of relatively high energies with application of only a simple negative chirp on the input pulses has been experimentally demonstrated. Although the fibers are multimode, the MFs can operate in what is effectively the single-mode regime, thus ensuring a near-diffraction-limited output beam. Comparison of the duration of the pulses delivered through a MF and that delivered through standard SMF under the same conditions shows that a MF can deliver pulses that are more than 10 times shorter. In addition, the high N.A. of these types of fiber could allow for efficient collection of fluorescence back through the fiber, which could prove useful for endoscopic multiphoton microscopy and fiber delivery of femtosecond pulses to conventional multiphoton microscopes.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method of identifying potential disease within a particular tissue of a plant or animal comprising the steps of:
    introducing into the tissue at least one input pulse of radiation through at least one large-core microstructured multimode optical fiber operating in a single-mode regime, wherein the at least one input pulse causes nonlinear activation of the tissue, and wherein the tissue emits at least one nonlinear signal in response to nonlinear activation;
    comparing said at least one nonlinear signal produced by said introducing to at least one nonlinear signal emitted by healthy tissue of the particular plant or animal under the same conditions used to carry out said introducing; and
    identifying the particular tissue of a plant or animal where the at least one nonlinear signal produced by said introducing differs from said at least one nonlinear signal emitted by said healthy tissue of the particular plant or animal under the same conditions used to carry out said introducing, as potentially diseased, wherein said at least one large-core microstructured multimode optical fiber has a numerical aperture of equal to or greater than 0.2.

2. The method according to claim 1, wherein said introducing is carried out with a large-core microstructured multimode optical fiber that is a large core step-index fiber.

3. The method according to claim 2, wherein said introducing is carried out with said large core step-index fiber which comprises a silica rod in air.

4. The method according to claim 1, wherein said introducing is carried out with said large-core microstructured multimode optical fiber that is terminally associated with a focusing device, wherein said focusing device is effective in decreasing the focal volume for delivering the output pulse of radiation from said fiber.

5. The method according to claim 4, wherein said introducing is carried out with said large-core microstructured multimode optical fiber that is terminally associated with a focusing device which comprises a lens or lens system.

6. The method according to claim 1, wherein said introducing is carried out with said large-core microstructured multimode optical fiber that is terminally associated with a scanning device under conditions effective to allow the scanning device to scan the nonlinear activation focal volume of the output pulse of radiation, thereby allowing an image formation technique to be used to form an image of the plant or animal tissue.

7. The method according to claim 6, wherein said image formation technique comprises laser scanning imaging.

8. The method according to claim 1, wherein the at least one input pulse of radiation is delivered substantially adjacent to the particular plant or animal tissue.

9. The method according to claim 1, wherein the at least one input pulse of radiation is delivered within the particular plant or animal tissue.

10. The method according to claim 1 further comprising:
    treating the particular plant or animal tissue with at least one photo-active agent prior to said introducing.

11. The method according to claim 1, wherein said at least one input pulse of radiation is generated by a laser.

12. The method according to claim 11, wherein said at least one input pulse of radiation is generated with a laser that is a mode-locked laser.

13. The method according to claim 1, wherein said at least one input pulse of radiation is pulsed at a pulse duration of between 10 and 1,000 femtoseconds.

14. The method according to claim 1, wherein said at least one input pulse of radiation is negatively prechirped.

15. The method according to claim 14, wherein said at least one input pulse of radiation is negatively prechirped using a dispersion compensation scheme.

16. The method according to claim 15, wherein said dispersion compensation scheme comprises using a grating pre-compensator to double-pass said at least one input pulse of radiation through a pair of diffraction gratings.

17. The method according to claim 1, wherein said introducing is carried out with at least one large-core microstructured multimode optical fiber that has a terminal end abutting a surface of the plant or animal tissue.

18. The method according to claim 1, wherein the at least one large-core microstructured multimode optical fiber is disposed within the plant or animal tissue.

19. The method according to claim 18, wherein said introducing is carried out with at least one large-core microstructured multimode optical fiber that constitutes or is associated with an optical biopsy needle.

20. The method according to claim 1, wherein the at least one large-core microstructured multimode optical fiber is disposed within a body cavity of the plant or animal.

21. The method according to claim 20, wherein said introducing is carried out with at least one large-core microstructured multimode optical fiber wherein said least one large-core microstructured multimode optical fiber is associated with an endoscope.

22. The method according to claim 20, wherein the body cavity is selected from the group consisting of mouth, colon, esophagus, stomach, intestine, bladder, uterus, vagina, lung, ovaries, and throat.

23. The method according to claim 1 further comprising:
    collecting radiation applied to the plant or animal tissue using one or more collection optical fibers.

24. The method according to claim 1, wherein the at least one nonlinear signal is selected from the group consisting of fluorescence produced from a nonlinear multiphoton absorption process, nonlinear scattering, and a non-fluorescence signal produced from a nonlinear multiphoton absorption process.

25. The method according to claim 1, wherein said introducing is carried out with said large-core microstructured multimode optical fiber that is associated with a multiphoton microscope under conditions effective to allow said at least one output pulse of radiation to be delivered to said multiphoton microscope.

26. A method of producing an image of an internal region of a particular tissue within a plant or animal comprising the steps of:
    introducing into the tissue at least one input pulse of radiation through at least one large-core microstructured multimode optical fiber operating in a single-mode regime, wherein the at least one input pulse causes nonlinear activation of the tissue, and wherein the tissue emits at least one nonlinear signal in response to nonlinear activation;
    collecting the at least one nonlinear signal under conditions effective to produce an image of the internal region, wherein said at least one large-core microstructured multimode optical fiber has a numerical aperture of equal to or greater than 0.2; and
    producing said image.

27. The method according to claim 26, wherein said introducing is carried out with said large-core microstructured multimode optical fiber that is a large core step-index fiber.

28. The method according to claim 27, wherein said introducing is carried out with said large core step-index fiber that comprises a silica rod in air.

29. The method according to claim 26, wherein said introducing is carried out with said large-core microstructured multimode optical fiber that is terminally associated with a focusing device, wherein said focusing device is effective in decreasing the focal volume for delivering the output pulse of radiation from said fiber.

30. The method according to claim 29, wherein said introducing is carried out with said large-core microstructured multimode optical fiber that is terminally associated with a focusing device which comprises a lens or lens system.

31. The method according to claim 26, wherein said introducing is carried out with said large-core microstructured multimode optical fiber that is terminally associated with a scanning device under conditions effective to allow the scanning device to scan the nonlinear activation focal volume of the output pulse of radiation, thereby allowing an image formation technique to be used to form an image of the plant or animal tissue.

32. The method according to claim 31, wherein said image formation technique comprises laser scanning imaging.

33. The method according to claim 26, wherein the at least one large-core microstructured multimode optical fiber is juxtaposed with a surface of the plant or animal tissue.

34. The method according to claim 26 further comprising:
treating the particular plant or animal tissue with at least one photo-active agent prior to said activating.

35. The method according to claim 26, wherein the at least one input pulse of radiation is generated by a laser.

36. The method according to claim 26, wherein the at least one input pulse of radiation is generated with a laser that is a mode-locked laser.

37. The method according to claim 26, wherein said at least one input pulse of radiation is pulsed at a pulse duration of between 10 and 1,000 femtoseconds.

38. The method according to claim 26, wherein said at least one input pulse of radiation is negatively prechirped.

39. The method according to claim 38, wherein said at least one input pulse of radiation is negatively prechirped using a dispersion compensation scheme.

40. The method according to claim 39, wherein said dispersion compensation scheme comprises using a grating precompensator to double-pass said at least one input pulse of radiation through a pair of diffraction gratings.

41. The method according to claim 26, wherein the at least one large-core microstructured multimode optical fiber is disposed within a body cavity of the plant or animal.

42. The method according to claim 26, wherein said introducing is carried out with at least one large-core microstructured multimode optical fiber that is associated with an endoscope.

43. The method according to claim 41, wherein the body cavity is selected from the group consisting of mouth, colon, esophagus, stomach, intestine, bladder, uterus, vagina, lung, ovaries, and throat.

44. The method according to claim 26, wherein said introducing is carried out with at least one large-core microstructured multimode optical fiber that is a bundle of large-core microstructured multimode optical fibers.

45. The method according to claim 26, wherein the at least one nonlinear signal is selected from the group consisting of fluorescence produced from a nonlinear multiphoton absorption process, nonlinear scattering, and a non-fluorescence signal produced from a nonlinear multiphoton absorption process.

46. The method according to claim 26, wherein said introducing is carried out with said large-core microstructured multimode optical fiber wherein said large-core microstructured multimode optical fiber is associated with a multiphoton microscope under conditions effective to allow said at least one output pulse of radiation to be delivered to said multiphoton microscope.

47. A method of detecting at least one nonlinear signal within a subject comprising the steps of:
applying radiation to an internal surface of the subject through at least one large-core microstructured multimode optical fiber operating in a single mode regime, each of which terminates in a tip proximate to the internal surface, wherein the said applying causes nonlinear activation of molecules within the internal surface and, as a result, the tissue emits at least one nonlinear signal proximate to the tip of the at least one large-core microstructured multimode optical fiber, wherein said applying comprises introducing at least one input pulse of radiation through said at least one large-core microstructured multimode optical fiber operating in a single mode regime, and wherein said at least one large-core microstructured multimode optical fiber has a numerical aperture of equal to or greater than 0.2 and
detecting the at least one nonlinear signal emitted from the tissue.

48. The method according to claim 47, wherein said applying is carried out with a large-core microstructured multimode optical fiber that is a large core step-index fiber.

49. The method according to claim 48, wherein said applying is carried out with said large core step-index fiber which comprises a silica rod in air.

50. The method according to claim 47, wherein said applying is carried out with a large-core microstructured multimode optical fiber wherein the tip of the large-core microstructured multimode optical fiber is terminally associated with a focusing device, wherein said focusing device is effective in decreasing the focal volume for delivering the output pulse of radiation from said fiber.

51. The method according to claim 50, wherein said applying is carried out with a large-core microstructured multimode optical fiber wherein the tip of the large-core microstructured multimode optical fiber is terminally associated with said focusing device which comprises a lens or lens system.

52. The method according to claim 47, wherein said applying is carried out with a large-core microstructured multimode optical fiber wherein the tip of the large-core microstructured multimode optical fiber is terminally associated with a scanning device under conditions effective to allow the scanning device to scan the nonlinear activation focal volume of the output pulse of radiation, thereby allowing an image formation technique to be used to form an image of the internal surface of the subject.

53. The method according to claim 52, wherein said image formation technique comprises laser scanning imaging.

54. The method according to claim 47, wherein the at least one large-core microstructured multimode optical fiber is inserted into the subject through an externally accessible body cavity of the subject.

55. The method according to claim 54, wherein said applying is carried out with the at least one large-core microstructured multimode optical fiber that is associated with an endoscope.

56. The method according to claim 54, wherein the body cavity is selected from the group consisting of mouth, colon, esophagus, stomach, intestine, bladder, uterus, vagina, lung, ovaries, and throat.

57. The method according to claim 47, wherein the at least one large-core microstructured multimode optical fiber is inserted into the subject through a penetrable surface of the body.

58. The method according to claim 47 further comprising:
imaging the internal surface of the subject after said applying.

59. The method according to claim 47 further comprising:
detecting disease in the internal surface of the subject after said applying.

60. The method according to claim 47 further comprising:
treating the subject with at least one photo-active agent prior to said applying.

61. The method according to claim 47, wherein the at least one input pulse of radiation is generated with a laser.

62. The method according to claim 61, wherein said at least one input pulse of radiation is generated with the laser that is a mode-locked laser.

63. The method according to claim 47, wherein said at least one input pulse of radiation is pulsed at a pulse duration of between 10 and 1,000 femtoseconds.

64. The method according to claim 47, wherein said at least one input pulse of radiation is negatively prechirped.

65. The method according to claim 64, wherein said at least one input pulse of radiation is negatively prechirped using a dispersion compensation scheme.

66. The method according to claim 65, wherein said dispersion compensation scheme comprises using a grating precompensator to double-pass said at least one input pulse of radiation through a pair of diffraction gratings.

67. The method according to claim 47 further comprising:
detecting histological and clinical composition, structure, metabolic state, and vitality in the internal surface of the subject after said applying.

68. The method according to claim 47 further comprising:
detecting functional response to physiological and pharmacological stimuli and disease states in the internal surface of the subject after said applying.

69. The method according to claim 47 further comprising:
detecting tissue or drug fluorescence excitation and emission spectra, luminosity, fluorescence lifetime, and temporal fluctuations in the internal surface of the subject after said applying.

70. The method according to claim 47, wherein the tissue is effective to produce second and third harmonics of illumination.

71. The method according to claim 47, wherein said applying is carried out with said large-core microstructured multimode optical fiber that is associated with a multiphoton microscope under conditions effective to allow said at least one output pulse of radiation to be delivered to said multiphoton microscope.

72. A method of detecting at least one nonlinear signal within a body of penetrable material comprising the steps of:
applying radiation to an internal region of the body of penetrable material through at least one large-core microstructured multimode optical fiber operating in a single mode regime, each of which terminates in a tip proximate to the internal region, wherein the said applying causes nonlinear activation of molecules within the internal region and, as a result, the tissue emits at least one nonlinear signal proximate to the tip of the at least one large-core microstructured multimode optical fiber, wherein said applying comprises introducing at least one input pulse of radiation through said at least one large-core microstructured multimode optical fiber operating in a single mode regime, and wherein said at least one large-core microstructured multimode optical fiber has a numerical aperture of equal to or greater than 0.2 and
detecting the at least one nonlinear signal emitted from the tissue.

73. The method according to claim 72, wherein said applying is carried out with said large-core microstructured multimode optical fiber that is a large core step-index fiber.

74. The method according to claim 73, wherein said applying is carried out with said large core step-index fiber which comprises a silica rod in air.

75. The method according to claim 72, wherein said applying is carried out with a large core step-index fiber wherein the tip of the large-core microstructured multimode optical fiber is terminally associated with a focusing device, wherein said focusing device is effective in decreasing the focal volume for delivering the output pulse of radiation from said fiber.

76. The method according to claim 75, wherein said applying is carried out with said large core step-index fiber wherein the tip of the large-core microstructured multimode optical fiber is terminally associated with a focusing device which comprises a lens or lens system.

77. The method according to claim 72, wherein said applying is carried out with the large-core microstructured multimode optical fiber that is terminally associated with a scanning device under conditions effective to allow the scanning device to scan the nonlinear activation focal volume of the output pulse of radiation, thereby allowing an image formation technique to be used to form an image of the internal region.

78. The method according to claim 77, wherein said image formation technique comprises laser scanning imaging.

79. The method according to claim 72, wherein said at least one large-core microstructured multimode optical fiber is inserted into the body of penetrable material.

80. The method according to claim 72 further comprising:
imaging the region of the body of penetrable material after said applying.

81. The method according to claim 72, wherein said at least one input pulse of radiation is generated with a laser.

82. The method according to claim 81, wherein said at least one input pulse of radiation is generated with the laser that is a mode-locked laser.

83. The method according to claim 72, wherein said at least one input pulse of radiation is pulsed at a pulse duration of about between 10 and 1,000 femtoseconds.

84. The method according to claim 72, wherein said at least one input pulse of radiation is negatively prechirped.

85. The method according to claim 84, wherein said at least one input pulse of radiation is negatively prechirped using a dispersion compensation scheme.

86. The method according to claim 85, wherein said dispersion compensation scheme comprises using a grating precompensator to double-pass said at least one input pulse of radiation through a pair of diffraction gratings.

87. The method according to claim 72, wherein the at least one nonlinear signal is selected from the group consisting of fluorescence produced from a nonlinear multiphoton absorption process, nonlinear scattering, and a non-fluorescence signal produced from a nonlinear multiphoton absorption process.

88. The method according to claim 72, wherein said applying is carried out with said large-core microstructured multimode optical fiber that is associated with a multiphoton microscope under conditions effective to allow said at least one output pulse of radiation to be delivered to said multiphoton microscope.

89. The method according to claim 72 further comprising: detecting tissue or drug fluorescence excitation and emission spectra, luminosity, fluorescence lifetime, and temporal fluctuations in the internal surface of the subject after said applying.

90. The method according to claim 72, wherein said body of penetrable material is selected from the group consisting of non-liquid material and liquid material.

91. The method according to claim 72, wherein said body of penetrable material is selected from the group consisting of a food product, a natural polymeric structure, a synthetic polymeric structure, a porous medium, and a drug candidate.

* * * * *